US006890542B2

(12) United States Patent
Mottram et al.

(10) Patent No.: US 6,890,542 B2
(45) Date of Patent: May 10, 2005

(54) LEISHMANIA VACCINE

(75) Inventors: Jeremy Charles Mottram, Bearsden (GB); Graham Herbert Coombs, Glasgow (GB)

(73) Assignee: University Court of the University of Glasgow, Glasgow (GB)

( * ) Notice: Subject to any disclaimer, the term of this patent is extended or adjusted under 35 U.S.C. 154(b) by 158 days.

(21) Appl. No.: 10/422,555

(22) Filed: Apr. 24, 2003

(65) Prior Publication Data

US 2004/0005326 A1 Jan. 8, 2004

Related U.S. Application Data

(63) Continuation of application No. 09/402,573, filed as application No. PCT/GB98/00994 on Apr. 3, 1998, now abandoned.

(30) Foreign Application Priority Data

Apr. 4, 1997 (GB) ............................................. 9706930

(51) Int. Cl.[7] ............................................ A61K 39/008
(52) U.S. Cl. ............................... 424/269.1; 424/184.1; 424/93.2; 424/93.21; 435/69.1; 435/71.1; 435/442; 435/375; 435/245; 435/243; 435/258.3; 435/947; 514/679
(58) Field of Search ............................. 424/184.1, 331, 424/47, 269.1, 93.2, 93.21; 435/69.1, 245, 243, 258.3, 71.1, 442, 375, 947; 514/679

(56) References Cited

U.S. PATENT DOCUMENTS

| | | | |
|---|---|---|---|
| 5,726,292 A | 3/1998 | Lowell | 530/403 |
| 5,827,671 A | 10/1998 | Matlashewski et al. | 435/7.22 |
| 5,863,775 A | 1/1999 | Atkinson et al. | 435/172.3 |
| 5,955,333 A | 9/1999 | Beverley et al. | 435/172.3 |
| 5,965,143 A | 10/1999 | Fasel et al. | 424/269.1 |
| 6,020,144 A | 2/2000 | Gueiros-Filho et al. | 435/7.22 |
| 6,133,017 A | 10/2000 | Matlashewski et al. | 435/258.3 |
| 6,162,638 A | 12/2000 | Papadopoulou et al. | 435/258.3 |
| 6,331,304 B1 | 12/2001 | Papadopoulou et al. | 424/269.1 |
| 6,403,081 B1 | 6/2002 | Papadopoulou et al. | 424/93.1 |
| 6,426,203 B1 | 7/2002 | Papadopoulou et al. | 435/172.1 |

FOREIGN PATENT DOCUMENTS

| | | |
|---|---|---|
| WO | 95/06729 | 3/1995 |
| WO | 98/44943 | 10/1998 |
| WO | 99/51264 | 10/1999 |

OTHER PUBLICATIONS

Omara–Opyene, Al et al, Molecular and Biochemical Parasitology, vol. 90, pp. 247–267, Dec. 1997.*
Cottnez–Detoefu, M. et al. "Vitro and In Vivo Effects of Interleukin 2 or Protozoan Parasite Leishmania." *Eur. J. Immunol.* 19:(3):487–491 (Mar. 1989).
Cox, F.E. "Designer Vaccines for Parasitic Diseases." *International Journal for Parasitology.* 27(10):1147–1157 (Oct. 1997) Abstract Only.

Denise, H. et al. "Expression of Multiple *CPB* Genes Encoding Cysteine Proteases Is Required for *Leishmania mexicana* Virulence In Vivo." *Infection and Immunity* 3190–3195 (Jun. 2003).
Lagardere B. "Future Vaccines in Parasitology." *Bulletin de la Societe de Pathologiec Exotique* 84(5 pt 5):926–934(1990) Abstract Only.
Bart, G et al. "Cathepsin B–like Cysteine Proteinase–Deficient Mutants of Leishmania Mexicana" *Molecular and biochemical parasitology.* 88(1–2):53–61 (Sep. 1997).
Bart, G et al. "Isolation of Imepe, a gene encoding a Leishmania mexicana cathepsin–B–like cysteine proteinase." *Molecular and Biochemical Parasitology.* 73(1–2):271–274 (Jul. 1995).
Boslego et a. *Vaccines and Immunotherapy.* Chapter 17: 211–223, (1991).
Ellis, RW. *Vaccines, New Technologies for making vaccines* Chapter 29:569–574, WB Saunders Company (1998).
Gueiros–Filho et al.; *Selection against the Dihydrofolate Reductase–Thymidylate Synthase (DHFR–TS) Locus as a Probe of Genetic Alternations in Leishmania major, Molecular and Cellular Biology,* 16:5655–5663 (Oct. 1996).
Mottram, JC et al. "A developmentally regulated cysteine proteinase gene of Leishmania mexicana" *Molecular microbiology* 6(14):1925–1932 (Jul. 1992).
Mottram, JC., et al. "The multiple cpb Cysteine Proteinase Genes of Leishmania Mexicana Encode Isoenzymes that Differ in their Stage Regulation and Substrate Preferen" *Journal of Biological Chemistry.* 272(22):14285–14293 (May 30, 1997).
Mottram, JC., et al. "Evidence from disruption of the Imcpb Gene Array of Leishmania Mexicana that Cysteine Proteina" *Proceedings of the National Academy of Sciences of the United States of America.* 93(12):6008–6013 (Jun. 11, 1996) (Abstract only).
Omara–Opyene, Al et al. *Molecular and Biochemical Parasitology.* 90:247–267 (1997).
Robertson et al.; *Parasite cysteine proteinases; Perspectives in Drug Discovery and Design,* 6:99–118 (Jun. 1996).
Souza, Ae et al. "Null Mutants for the Imcpa Cysteine Proteinase Gene in Leishmania Mexicana" *Molecular and Biochemical Parasitology.* 63(2):213–220 (Feb. 1994).
Souza, AE et al. "Characterization of a multi–copy gene of a major stage specific cysteine proteinase of Leishmania mexicana" *FEBS Letters* 311(2):124–127. (Oct. 19, 1992).

(Continued)

Primary Examiner—Lynette R.F. Smith
Assistant Examiner—Ginny Allen Portner
(74) Attorney, Agent, or Firm—Myers Bigel Sibley & Sajovec, P.A.

(57) ABSTRACT

The present invention relates to the use of a live mutant *Leishmania* in the preparation of a vaccine and to vaccine formulations for use in immunizing mammals, such as dogs and/or humans. The mutant *Leishmania* comprises at least one defective cysteine proteinase gene.

16 Claims, 10 Drawing Sheets

OTHER PUBLICATIONS

Titus et al.; *Development of a safe live Leishmania vaccine line by gene replacement*, Proc. Natl Acad Sci USA 92:10267–10271 (Oct. 1995).

Tobin et al.; *Transfected Leishmania Expressing Biologically Active IFN-y[1]*, The Journal of Immunology, 150, No. 11:5059–5069 (Jun. 1993).

Wolfram, M et al. "Antigen presentation by Leishmania mexicana–infected macrophages: activation of helper T cells specific for amastigote cysteine proteinases requires" *European Journal of Immunology.* 25(4):1094–1100. (Apr. 1995).

* cited by examiner

Figure 8

```
   1  ATGGCGCGCC CCAACTGCTT TTTGTTTGCG ATAGTGGTGA CTATCCTGTT
  51  CGTGGTGTGC TACGGTTCCG CTCTCATCGC CCAGACACCT CTCGGTGTCG
 101  ACAACTTCAT TGCCTCAGCG CATTACGGAC GCTTTAAGAA GCACCACGGC
 151  AAGGCCTTCG GCGAGGACGC CGAGGAGGGT CGCCGCTTCA ATGCCTTCAA
 201  CCAGAACATG CAGACAGCCT ACTTCCTCAA CGCGCACAAC CCACACGCGC
 251  ACTACGACGT GTCCGGCAAG TTCGCAGACC TCACCCCCA GGAGTTCGCC
 301  AAGCTGTACC TAAACCCCAA CTACTACGCG CGCCACGGCA AGGATTACAA
 351  GGAGCACGTG CACGTCGACG ACAGCGTCCG CAGTGGTGTG ATGTCGTTGG
 401  ACTGGCGTGA GAAGGGTGCC GTGACACCGG TGAAGAACCA GGGAATGTGC
 451  GGCTCGTGCT GGGCCTTCTC CGCCATTGGC AACATTGAAG GCCAGTGGGC
 501  TTTGAAAAAC CACTCGCTGG TTTCGCTGTC GGAGCAGATG CTCGTGTCAT
 551  GCGACGACAT CGATGATGGG TGCAACGGCG GCTGATGGA CCAGGCAATG
 601  GAATGGATCA TCCACCATCA CAACGGCACT GTGCCCACGG AGGAAAGCTA
 651  CCCCTACGCC TCTGCCGGCG GCACGAGGCC GCCGTGCCAT GACAAAGGCA
 701  ACGTTGGCGC CAGAATCGGC GGTTACATGT CCCTGCCGCA TGACGAGAAG
 751  GAGATCGCGG CTTATGTGGA AAGAACGGC CCCGTCGCCG TCGCCGTCGA
 801  CGCGACAACC TGGCAGCTGT ACTTTGGCGG TGTGGTCACC CTCTGCTTCG
 851  GGTGGTCGCT CAACCACGGT GTGCTCGTTG TCGGCTTCAA CAGAGACGCG
 901  AAACCGCCGT ACTGGATCGT GAAGAACTCG TGGGGCACCT CGTGGGGTCA
 951  GAACGGGTAC ATCCGCCTTG CCATGGGCAG CAACCAGTGC TTGCTGAAGA
1001  ATTACGCCGT GACGGCCACG ATAGACGACT CCAACACCTC CCACGTGCCG
1051  ACGACAACGG CCTAG
```

Figure 9. Predicted protein sequence of L. infantum CPA

MARRNCFLFA IVVTILFVVC YGSALIAQTP LGVDNFIASA HYGRFKHGHG

KAFGEDAEEG RRFNAFKQNM QTAYFLNAHN PHAHYDVSGK FADLTPQEFA

KLYLNPNYYA RHGKDYKEHV HVDDSVRSGV MSLDWREKGA VTPVKNQGMC

GSCWAFSAIG NIEGQWALKN HSLVSLSEQM LVSCDDIDDG CNGGLMDQAM

EWIIHHHNGT VPTEESYPYA SAGGTRPPCH DKGNVGARIG GYMSLPHDEK

EIAAYVEKNG PVAVAVDATT WQLYFGGVVT LCFGWSLNHG VLVVGFNRDA

KPPYWIVKNS WGTSWGENGY IRLAMGSNQC LLKNYAVTAT IDDSNTSHVP

TTTA

Figure 10  Nucleotide Sequence of *cpb* from *Leishmania infantum*

```
   1  ATGGCGACGT CGAGGGCCGC TCTTTGCGCT GTTGCGGTTG TGTGCGTGGT
  51  GCTTGCGGCT GCCTGCGCGC CCGCGCGCGC GATATACGTG GGGACGCCGG
 101  TTGCTGCGCT GTTCGAGGAG TTCAAGCGGA CGTACCGGCG CGCGTACGGG
 151  ACGGTCGCCG AGGAGCAGCA GCGGCTGGCG AACTTCGAGC GCAACCTGGA
 201  GCTGATGCGC GAGCATCAGG CGAGGAACTC ACACGCGAGG TTCGGGATCA
 251  CGAAGTTCTT CGACCTGTCG GAGGCGGAGT TCGCCGCGCG CTACCTGAAC
 301  GGCGCCGCGT ACTTCGCAGC GGCGAAGCAG CACGCCGGCC AGCACTACCG
 351  CAAGGCGCGC GCCGACTTCT CGGCGGTGCC TGATGCGGTG GACTGGCGCA
 401  AGAAGGGCGC CGTGACGCCG GTGAAGGATC CGXXXXXXXX XXXXXXXXXX
 451  XXXXXXXXXX XXXXXXXXXX XXXXXXXXXX XXXXXXXXXX XXXXXXXXXX
 501  XXXXXXXXXX XXXXXXXXXX XXXXXXXXXX XXXXXXXXXX XXXXXXXXXX
 551  XXXXXXXXXX XXXXXXXXXX XXXXXXXXXX XXXXXXXXXX XXXXXXXXXX
 601  XXXXXXXXXX XXXXXXXXXX XXXXXXXXXX XXXXXXXXXX XXXXXXXXXX
 651  XXXXXXXXXX XXXXXXXXXX XXXXXXXXXX XXXXXXXXXX XXXXXXXXXX
 701  XXXXXXXXXX XXXXXXXXXX XXXXXXXXXX XXXXXXXXXX XXXXXXXXXX
 751  XXXXXXXXXX XXXXXXXXXX XXXXXXXXXX XXXXXXXXXX XXXXXCCAG
 801  CTCCTTCATG TCCTACCAGA GCGGCGTGCT GACCAGCTGC GCTGGGGATG
 851  CTCTGAACCA CGGCGTGCTG CTCGTTGGGT ACAACAGGAC TGGTGAGGTT
 901  CCGTACTGGG TGATCAAGAA CTCGTGGGGT GAGGACTGGG GCGAGAACGG
 951  CTACGTGCGC GTGACCATGG GGGTGAACGC GTGCCTGCTC ACTGAATACC
1001  CCGTGTCCGC GCATGTGCCG CAGAGTCCCA CCCTGGCCC GAGCACGGAG
1051  AGCGAGGAGC GCGCTCCAAA ACGGGTGATG GTGGAGCAGA TAATCTGCAC
1101  GGATATGTAC TGCAGGGAGG GGTGCAGGAA GACTCTTCTC ACCGCGAACG
1151  TGTGCCAGCT GAACGGGGGA GGCGGCTCCT CTATGACCAA GTGCAGTCCG
1201  CACAAGGTGC TGATGTGCAC GTACTCGAAC CCTCGTTGCT TTGGTCCGGG
1251  GCTTTGCCTC GAGACTCCTG ATGGTAAGTG TGCGCCGTAC TTCTTGGGCT
1301  CGGTCACTAA CACCTGCCAG TACACGTAG
```

Figure 11  Predicted protein sequence of *L.infantum* CPB

```
1                                                                50
MATSRAALCA VAVVCVVLAA ACAPARAIYV GTPAAALFEE FKRTYERAVG 51                                                               100
TVAEEQQRLA NFERNLELMR EHQARNPHAR FGITKFFDLS EAEFAARYLN 101                                                              150
GAAYFAAAKQ HAGQHYRKAR ADLSAVPDAV DWRKKGAVTP VKDFXXXXXX 151                                                              200
XXXXXXXXXX XXXXXXXXXX XXXXXXXXXX XXXXXXXXXX XXXXXXXXXX 201                                                              250
XXXXXXXXXX XXXXXXXXXX XXXXXXXXXX XXXXXXXXXX XXXXXXXXXX 251                                                              300
XXXXXXXXXX XXXXXXSSFM SYQSGVLTSC AGDALNHGVL LVGYNRTGEV 301                                                              350
PYWVIKNSWG EDWGENGYVR VTMGVNACLL TEYPVSAHVP QSPTPGPSTE 351                                                              400
SEERAPKRVM VEQIICTDMY CREGCMKTLL TANVCQLNGG GGSSNTKCGP 401                                                              450
HKVLMCTYSN PRCFGPGLCL ETPDGKCAPY FLGSVTNTCQ YT*
```

LEISHMANIA VACCINE

CROSS-REFERENCE TO RELATED APPLICATIONS

The present application is a continuation application of U.S. patent application Ser. No. 09/402,573 filed Oct. 25, 1999, which claims priority to PCT/GB98/00994, filed Apr. 3, 1998, which claims priority to United Kingdom Application No. 9706930.6, filed Apr. 4, 1997, the disclosures of which are incorporated herein by reference in their entireties.

The present invention relates to a *Leishmania* vaccine, more particularly an attenuated live *Leishmania* vaccine for use in immunising mammals, such as dogs and/or humans.

The World Health Organisation estimates that *Leishmania* is prevalent in 88 Countries of the world with a population at risk estimated at 367 million with 400,000 deaths a year. *Leishmania* species also infect other mammals. In many countries, leishmaniasis in dogs is an important problem. The close proximity of humans and dogs, and the evidence that dogs and other mammals act as reservoirs of human infection, have meant that there has been widespread killing of dogs as a disease control measure. This is clearly unsatisfactory, but also has not made a significant impact on the spread of human disease. Thus the development of a vaccine would be of immense benefit to both humans and dogs.

Leishmaniasis encompasses a large spectrum of clinical diseases, which depending upon the parasite species and the host immune response, can have various outcomes. In humans these clinical syndromes include single cutaneous lesions, which may or may not spontaneously heal, and more severe cases associated with metastasis to other cutaneous or mucocutaneous sites, as well as visceralization of the parasites leading to a fatal infection if not properly treated. Present understanding of the factors that lead to this diversity of clinical symptoms has, in large part, come from studies using murine models (reviewed Alexander & Russell, 1992; Liew & O'Donnell, 1993). While the vast majority of mouse strains develop healing lesions when infected subcutaneously with *L. major*, virtually all develop non-healing lesions full of parasites when infected subcutaneously with *L. mexicana* (Roberts et al., 1989; Roberts et al., 1990). Furthermore, as *L. mexicana* will visceralise from primary lesions in mice under the influence of genetic controls originally identified from studies of *L. donovani*, this parasite in mice offers an excellent model system for putative vaccine studies against disseminating disease in a variety of susceptible genotypes.

In areas such as Southern Europe and South America where the causative agents of visceral leishmaniasis are *L. infantum* and *L. chagasi*, respectively, the domestic dog represents the major animal reservoir of the disease. The incidence of canine leishmaniasis throughout Southern Europe can range from 10% to as much as 60% (Dye et al., 1992, 1993). Once a dog develops symptoms the outcome is invariably fatal (Bray 1982; Slappendel 1988). A major question remaining to be addressed, however, is whether vaccination can effectively induce a cellular immune response and protection against canine leishmaniasis.

It is the general consensus of opinion that acquired protective immunity against murine leishmaniasis, both cutaneous and visceral, is dependent on the ability to mount an IL-12 driven CD4+ T Helper 1-type response (reviewed Bogdan et al., 1996). This lymphocyte subset produces IFN-γ which mediates protection by up-regulating macrophage inducible nitric oxide synthase (iNOS) expression and NO production which is microbicidal for the parasites (Liew & O'Donnell, 1993). Consequently, neutralisation of IL-12 or IFN-γ, or inhibition of NO production, results in disease exacerbation (reviewed Bogdan et al., 1996).

The immunological pathways leading to the development of non-healing progressive disease are less well characterised and more contentious. Thus, although a large number of studies have indicated that susceptibility to *L. major* (reviewed Liew & O'Donnell 1993; Bogdan et al., 1996), *L. mexicana* (Satoskar et al., 1995) and *L. amazonensis* (Afonso & Scott, 1993) is related to developing a Th2 response and IL-4 production with down-regulation of Th1-associated activities, further studies on these species, as well as *L. donovani*, suggest that the inability to mount a Th1 response rather than the presence of Th2 response may determine susceptibility (Kaye et al., 1991; Satoskar & Alexander, 1995; Noben-Trauth et al., 1996). Nevertheless, recent studies using IL-4 gene-deficient mice from a number of genetic backgrounds have demonstrated a requirement for IL-4 in *L. mexicana* disease progression. In the absence of this cytokine, lesions did not develop at the site of subcutaneous inoculation (Satoskar et al., 1995).

Proteinases have been shown to play an important role in the pathogenicity of parasitic protozoa (see Robertson et al., 1996; Coombs & Mottram, 1997). *L. mexicana* contains multiple, highly active cysteine proteinases (CPs), many of which are stage-regulated. The present inventors have characterised biochemically a large number of CPs, many of which are stage-specific (reviewed Coombs & Mottram, 1997), and have isolated three *L. mexicana* CP genes; cpa, a single copy gene encoding a non-abundant cathepsin L-like CP (Mottram et al., 1992); cpb, a multicopy gene which encodes the major cathepsin L-like CPs of amastigotes (Souza et al., 1992); and cpc, a single copy gene encoding a cathepsin B-like CP (Bart et al., 1995).

In *Leishmania*, genes can be deleted by homologous recombination using gene-specific targeting DNA linked to an antibiotic resistance gene, such as hyg or neo, providing positive selection. cpa null mutants have been generated, but have no detectable phenotype (Souza et al., 1994). cpb null mutants, however, were found to have a virulence phenotype (Mottram et al., 1996).

All life-cycle stages of the cpb null mutant can be cultured in vitro, demonstrating that the gene is not essential for growth or differentiation of the parasite under these conditions. The null mutant, however, exhibits a marked phenotype affecting virulence—its infectivity to macrophages is reduced 5–10 fold. Data suggest that the mutants can only survive in a subpopulation of macrophages, but the parasites that successfully infect these macrophages grow normally. cpa/cpb double null mutants were also created using four antibiotic selectable markers, hyg, ble, sat and pur (Mottram et al., 1996). These had a similar phenotype to the cpb null mutant in terms of macrophage infectivity, showing that cpa does not compensate for the loss of cpb functions in this phenotypic test.

It was also observed that subcutaneous lesions in BALB/c mice resulting from inoculation of the cpb null mutant appeared considerably later than those due to the wild-type parasites, but nevertheless lesions were observed (Mottram et al, 1996).

The development of a live *Leishmania* vaccine line by gene replacement has previously been studied. A conditional auxotroph of *L. major* in which the dihydrofolate reductase-thymidylate synthase (dhfr-ts) gene had been deleted, was evaluated for its usefulness as a potential vaccine. The dhfr-ts mutant was found to be an effective vaccine line for immunizing against cutaneous *Leishmania* and was shown to be incapable of establishing a persistent infection or causing disease in the most susceptible strains of mice tested. However, mild infections were observed after subsequent parasite challenge, which is generally undesirable for a vaccine (Titus et al., 1995).

It is among the objects of the present invention to provide an improved *Leishmania* vaccine. More particularly it is a preferred object of the present invention to provide a live attenuated *Leishmania* vaccine which does not substantially display any disease manifestation after inoculation and/or after subsequent parasite challenge.

In one aspect the present invention provides the use of a mutant *Leishmania* in the preparation of a vaccine, wherein the mutant *Leishmania* comprises at least one defective cysteine proteinase gene type, such that the mutant *Leishmania* is substantially incapable of expressing a functionally active form of said at least one cysteine proteinase.

Preferably the mutant *Leishmania* comprises two or more defective cysteine proteinases and thus is substantially incapable of expressing functionally active forms of said two or more cysteine proteinases.

A further aspect of the invention relates to the vaccine itself.

The mutant *Leishmania* is preferably one which is substantially incapable of causing any disease manifestation, such as lesion formation, to a mammal, and/or there is no disease manifestation in a mammal which has been inoculated with the mutant *Leishmania* and subsequently challenged with a further disease causing *Leishmania*. However, the mutant *Leishmania* must at least be able to survive in a mammalian host for a sufficient length of time, so that an immune response may be elicited thereto. While the present description refers mainly to the use of promastigotes in the preparation of a vaccine, it is to be understood that pure amastigotes or amastigotes in mammalian cells may be used as alternatives.

The mutant *Leishmania* may be selected from all species of *Leishmania* including *L. braziliensis, L. peruviana, L. guyanensis, L. mexicana, L. major, L. amazonensis, L. infantum, L. chagasi* and *L. donovani*, Preferably the mutant *Leishmania* displays cross-protection to other *Leishmania* species. Thus, for example, a mammal immunised with a mutant *L. mexicana* as described herein may not only provide protection to infection from disease-causing *L. mexicana* but also to other disease-causing species, as listed above.

A "defective cysteine proteinase gene" is one which is substantially incapable of encoding for a native cysteine proteinase or a functional equivalent thereof. In line with common terminology cysteine proteinase is understood to relate to and include the proteolytic enzymes containing a nucleophilic cysteine as a member of the catalytic machinery. This is described in detail in Barrett and Rawlings 1996. Thus, a "defective cysteine proteinase gene" means that the cysteine proteinase gene has been modified by a deletion, insertion, substitution (or other change in the DNA sequence such as rearrangement) such that the cysteine proteinase gene is generally incapable of expressing a functionally competent cysteine proteinase from said gene. It will be appreciated that modification may also extend to the promoter and/or termination region of the gene, providing that the result is that a functionally competent cysteine proteinase from the particular gene is not expressed.

The "defective cysteine proteinase gene may" however be capable of expressing a defective cysteine proteinase which is inactive enzymically. Such a defective cysteine proteinase may however be antigenlc or immunogenic, such that a host may elicit an immune response to the defective cysteine proteinase.

If the mutant is for example a *L. mexicana* mutant then said at least one cysteine proteinase gene may be selected from, for example, cpa, a single copy gene encoding a non-abundant cathepsin L-like CP; cpb, a multicopy gene which encodes the major cathepsin L-like CPS of amastigotes; and cpc, a single copy gene encoding a cathepsin B-like CP.

The present inventors have now also identified corresponding genes to cpa and cpb in *L. infantum* and their corresponding proteins (see FIGS. 8–11), such that *L. infantum* cysteine proteinase mutants may also be produced as described herein and used in the preparation of a vaccine.

Thus, in a further aspect the present invention provides a vaccine formulation comprising a mutant *L. infantum* wherein at least one cysteine proteinase gene has been made defective as described herein. Preferably the mutant *L. infantum* comprises two or more defective cysteine proteinases.

CP genes of the present invention which are subsequently incapable of expressing a functionally competent cysteine proteinase may be rendered dysfunctional by any one or more ways for example:

(i) A deletion of the entire cysteine proteinase coding region of the cp gene from a wild type *Leishmania* genome. The deletion should be such so as not to substantially affect the expression of other gene products from the *leishmania* parasite genome.

(ii) A deletion of a portion of the cysteine proteinase coding region from a wild type *Leishmania* genome. A "portion of the cysteine proteinase coding region" means a polynucleotide fragment which by its deletion from the CP coding region is sufficient to render any CP or fragment or fragments thereof encoded and/or expressible thereby, substantially incapable of a physiological activity attributable to that of a functional CP produced by a wild type parasite. The deleted portion of cp may compromise a deletion of a small number of nucleotides, for example, 1, 2 or more nucleotides. Such deletions within the cp gene can be achieved using recombinant DNA technology. Thus, the translational open reading frame (ORF) for a cp can be altered resulting in the production of a protein which lacks the physiological functionality or functional competence of a CP derived from wild type *Leishmania*. The skilled addressee will also appreciate that such deletions in the translational ORF of the cp gene may also give rise to a dysfunctional gene which is substantially incapable of coding for a functionally competent CP, truncated CP or polypeptide fragment thereof. Such proteins/polypeptides, if produced, generally lack the functional competence typical of the CP enzyme.

(iii) The deletion of the or a portion of the cop gene as described in (i) or (ii) above will leave a "gap" in the cp gene. A suitable polynucleotide such as a gene or gene fragment thereof may be inserted into the "gap". Gene insertions can include genes which express polypeptides capable of augmenting an immune response, such as mammalian cytokines, for example, γ interferon or other genes such as marker genes. Suitable marker genes may include but are not restricted to genes encoding enzymes, for example thymidine kinase, or genes encoding antibiotic resistance to such as, puromycin, tunicamycin, hygromycin, neomycin, phleomycin, nourseothricin and the like. Generally these genes, if any, may be employed in a cp deletion. Mutants of the invention should be such so as not to cause substantial deleterious or long lasting side-effects to a recipient animal.

It is preferred however that antibiotic resistance genes are not present in cp-mutant cell lines to be used clinically for vaccination. Thus, it is preferred to utilise a system which generates drug resistance marker-free mutants. Such a system may involve sequential rounds of targeted gene disruption using positive and negative selection. In the generation of CP double or multiple null mutants, typically, each of said at least two cp genes will be targeted for disruption independently and subsequently multiple mutants will be generated. The hygromycin (hyg) gene may be used as a positive selectable marker for the antibiotic hygromycin. The viral HSV thymidine kinase gene (tk) may be used as a negative selectable marker in conjunction with the drug ganciclovir (Lebowitz, 1994).

For example, wild type *Leishmania* may be transfected with a construct containing both the hyg and tk genes arranged in tandem in order to delete one allele of a cp gene. Selection with hygromycin will allow transformants to be selected in which the particular cp gene has been deleted as, for example, described previously (Mottram et al 1996). A second round of transfection would then be performed with a "null targeting fragment", containing cp flanking DNA, that will delete the hyg/tk DNA that has been integrated into the cp locus. Cells in which the tk gene remains may then be killed by the ganciclovir drug, whereas mutants in which the cp gene and the drug markers have been deleted will grow. In this manner one allele of the cp gene will have been deleted and no exogenous DNA will remain in the cp locus. The procedure will then be repeated for the second cp allele as *Leishmania* is diploid, to produce a cp-null mutant. The entire procedure may then be repeated if necessary in order to produce a viable cp double null mutant and repeated again to produce viable cp triple null mutants etc.

In a preferment there is provided a *Leishmania* cp double or triple null mutant comprising deletions in said cp regions within the *Leishmania* genome. The deletion should be such that coding sequences for other gene products of the *Leishmania*, upstream and/or downstream from the cp domains, are not substantially affected. That is to say that other gene products ordinarily having an immunogenic function and which are expressed in *Leishmania* substantially retain their immunogenic function.

The deletion generally has to be made in said cp genes in positions such that any mutant *Leishmania* within a host cell retains a sufficient immunogenic function to elicit at least a cellular immune response (such as cytotoxic T-cell response more preferably a Th1 cell response) in a host animal, such as a dog or human. If the prophylactic and/or therapeutic effect of an appropriate *Leishmania* mutant of the present invention is to be augmented, an appropriate adjuvant protein or polypeptide, such as a cytokine, for example, γ interferon (γ IFN) can also be employed as a component of a vaccine or pharmaceutical composition of the invention.

Optionally, such cp-null *Leishmania* mutants may be further modified to express a dysfunctional form of a cysteine proteinase, such as the cysteine proteinase(s) which is/are not expressed by the mutant. Thus, the mutant may express a cysteine proteinase which is enzymically inactive, but which is antigenic or immunogenic. For example, to produce an inactive cysteine proteinase the active site cysteine of the cp gene can be changed by site-directed mutagenesis to a glycine residue. This mutation results in the production of a full length cysteine proteinase enzyme that is functionally inactive. The gene encoding the inactive cysteine proteinase can then be re-introduced into a cp-null mutant by homologous recombination using unique sequence that flank the cp gene. Similar dysfunctional cysteine proteinases can be produced by further mutagenesis as described for example in Example 5.

In a further embodiment of the invention there is provided a host cell comprising a cp-null *Leishmania* mutant of the present invention. The host cell may for example be a macrophage or similar cell type known to those skilled in art.

cp-null *Leishmania* mutants of the present invention may be applied directly to the cells of an animal in vivo, or by in vitro infection of cells taken from the said animal, which cells are then introduced back into the animal. *Leishmania* cp-null mutants may be delivered to various tissues of the animal body including muscle, skin or blood cells thereof. The *Leishmania* cp-null mutant may be injected into for example, muscle or skin using a suitable syringe.

cp-null *leishmania* mutants for injection may be prepared in unit dosage form in ampoules, or in multidose containers. The parasites may be present in such forms as suspensions, solutions, or emulsions in oily or preferably aqueous vehicles. For any parenteral use, particularly if the formulation is to be administered intravenously, the total concentration of solutes should be controlled to make the preparation isotonic, hypotonic, or weakly hypertonic. Nonionic materials, such as sugars, are preferred. Any of these forms may further comprise suitable formulatory agents, such as starch or sugar, glycerol or saline. The compositions per unit dosage, whether liquid or solid, may contain from 0.1% to 99% of parasite material.

In a further embodiment of the invention there is provided a vaccine against *Leishmania* comprising a cp-deficient *Leishmania* mutant. The vaccine of the invention may optionally include a further compound having an immunogenic function such as a cytokine, for example, γ interferon; or a disfunctional cysteine proteinase. The disfunctional cysteine proteinase may for example be obtained from the cpa, cpb and cpc genes of *L. mexicana* as well as the corresponding cpa and cpb genes of *L. infantum* as disclosed herein (see FIGS. 8 and 10).

The present invention therefore also relates to the use of *L. infantum* cpa and cpb genes (see FIGS. 8 and 10) and to the corresponding proteins expressed therefrom (see FIGS. 9 and 11).

The dysfunctional cysteine proteinase(s) may be provided in the vaccine as a purified or semi-purified protein or expressed by other carriers such as bacteria, viruses, protozoa, as well as the particular mutant(s) *Leishmania* of the present invention.

In a preferred presentation, the vaccine can also comprise an adjuvant. Adjuvants in general comprise substances that boost the immune response of the host in a non-specific manner. A number of different adjuvants are known in the art. Examples of adjuvants may include Freund's Complete adjuvant, Freund's Incomplete adjuvant, liposomes, and niosomes as described in WO 90/11092, mineral and non-mineral oil-based water-in-oil emulsion adjuvants, cytokines, short immunostimulatory polynucleotide sequences for example in plasmid DNA containing CpG dinucleotides such as those described by Sato Y. et al. (1996); Kreig A. M. (1996).

In addition, the vaccine may compromise one or more, suitable surface-active compounds or emulsifiers, e.g. Span or Tween.

In a further aspect of the invention there is provided the use of a cp-deficient *Leishmania* mutant as described herein for the manufacture of a vaccine for the prophylaxis and/or treatment of Leishmaniasis. Most preferably, the use is in dogs or humans.

In a further aspect of the invention there is provided a method of treating animals which comprises administering thereto a vaccine composition comprising a cp-deficient *Leishmania* mutant as described herein to animals in need thereof. Preferably, the animals are dogs or humans. Naturally, the vaccine formulation may be formulated for administration by oral dosage, by parental injection or otherwise.

The invention also provides a process for preparing a *Leishmania* vaccine, which process comprises admixing a cp-deficient *Leishmania* mutant as herein described with a suitable carrier or adjuvant.

The mode of administration of the vaccine of the invention may be by any suitable route which delivers an immunoprotective amount of the parasite of the invention to the subject. However, the vaccine is preferably administered parenterally via the intramuscular or deep subcutaneous routes. Other modes of administration may also be employed, where desired, such as oral administration or via other parental routes, i.e., intradermally, intranasally, or intravenously.

Generally, the vaccine will usually be presented as a pharmaceutical formulation including a carrier or excipient, for example an injectable carrier such as saline or pyrogenic water. The formulation may be prepared by conventional means. It will be understood, however, that the specific dose level for any particular recipient animal will depend upon a variety of factors including age, general health, and sex; the time of administration; the route of administration; synergistic effects with any other drugs being administered; and the degree of protection being sought. Of course, the administration can be repeated at suitable intervals if necessary.

Embodiments of the invention will now be illustrated by way of the following Figures and Examples; wherein FIG. 1 shows cutaneous lesion growth in BALB/c mice infected with $5 \times 10^6$ stationary phase *L. mexicana* promastigotes of wild type (•), Δcpa (○), or Δcpb (Δ). The data are means from each group of mice; (the symbol Δ is used herein to refer to a particular mutant which is defective in the named gene(s));

Figure 5A:
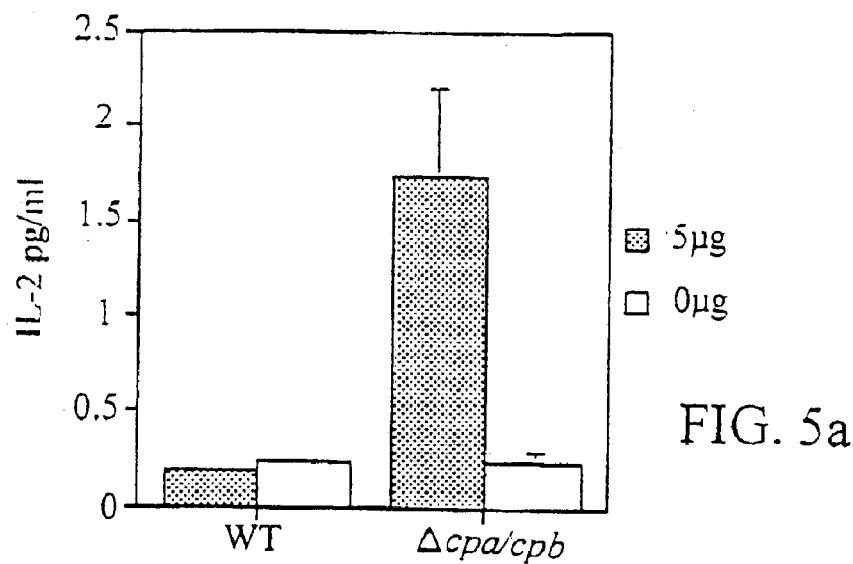
Figure 5B:
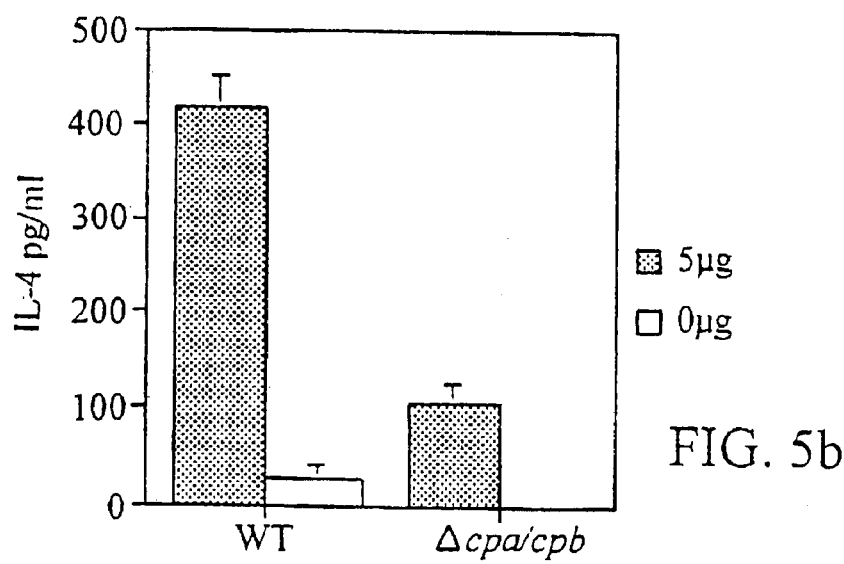
Figure 5C:
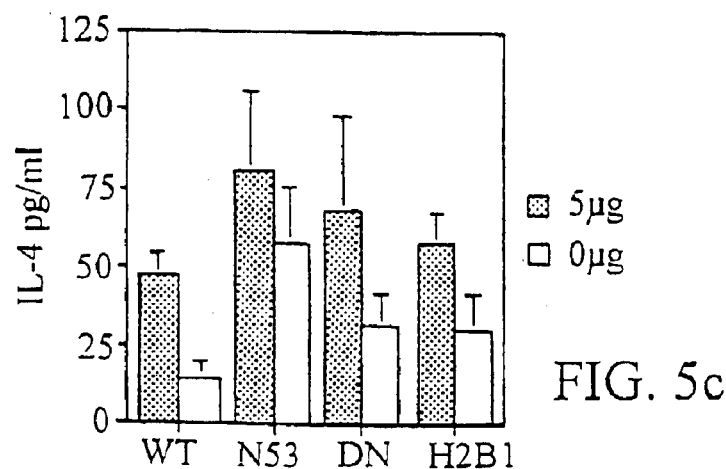
Figure 6A:
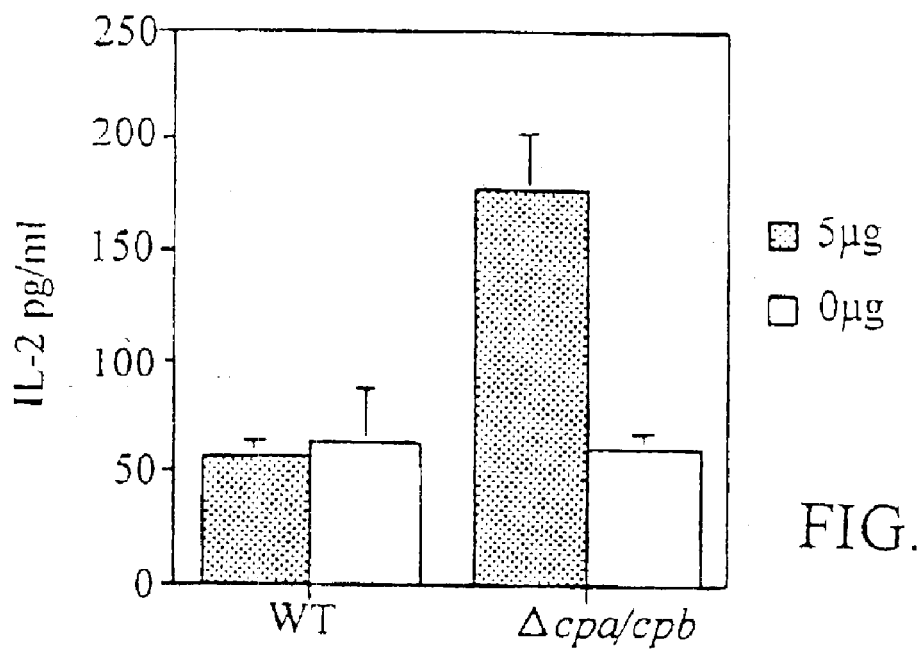
Figure 6B:
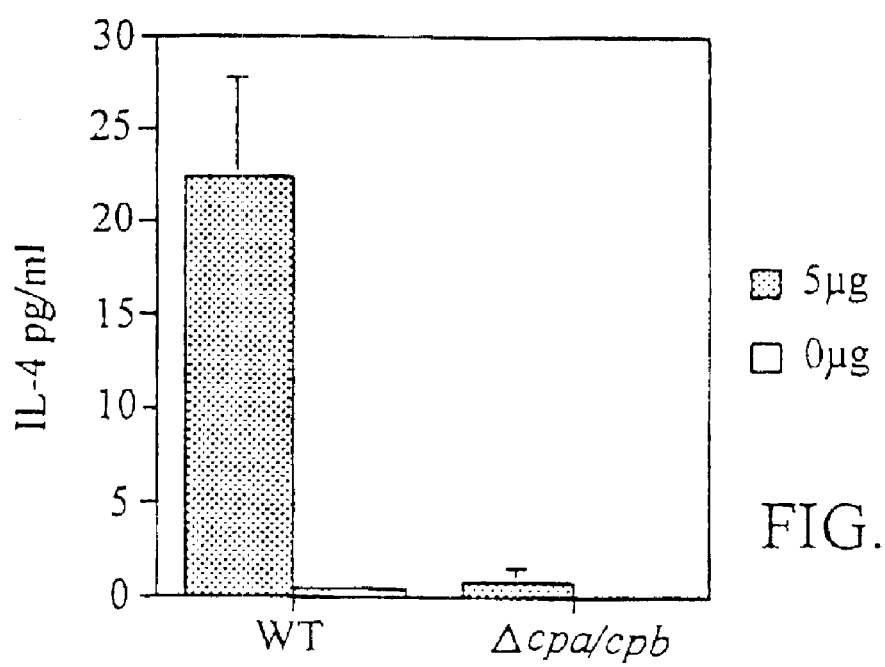
Figure 6C:
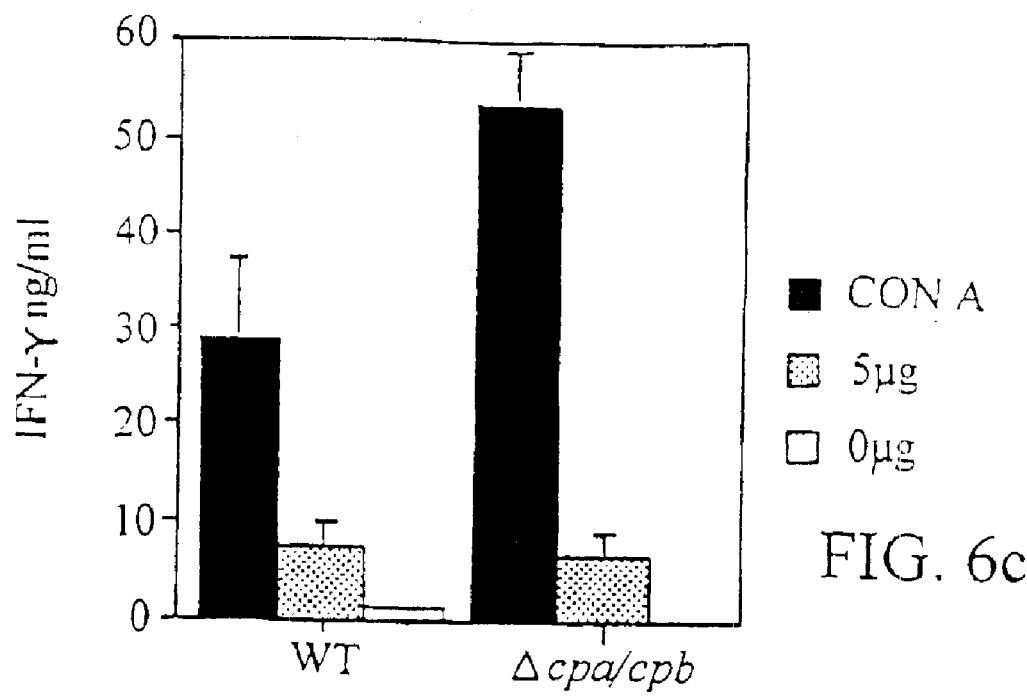
Figure 6D:
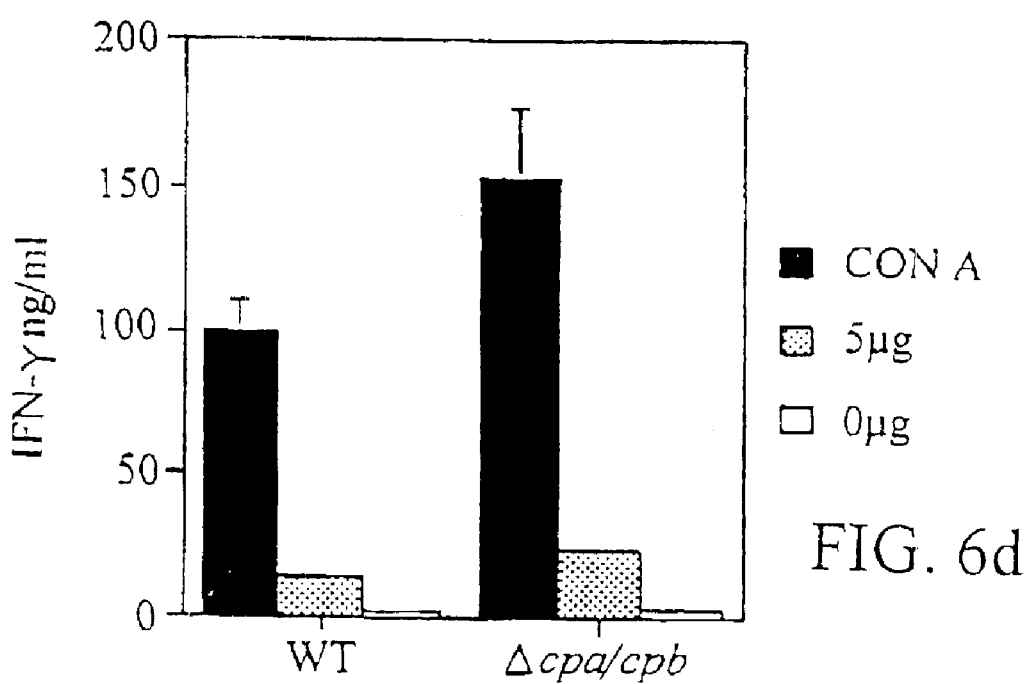
Figure 7A:
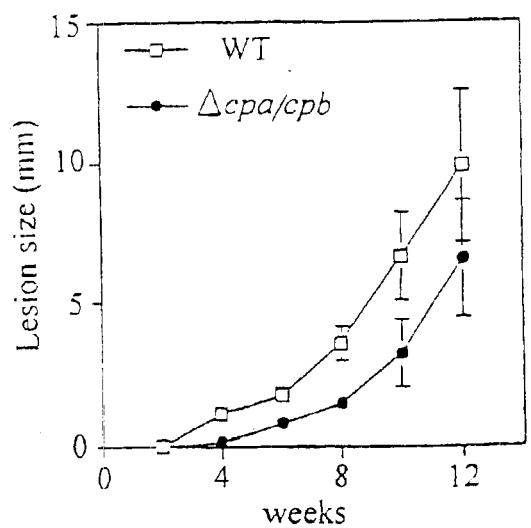
Figure 7B:
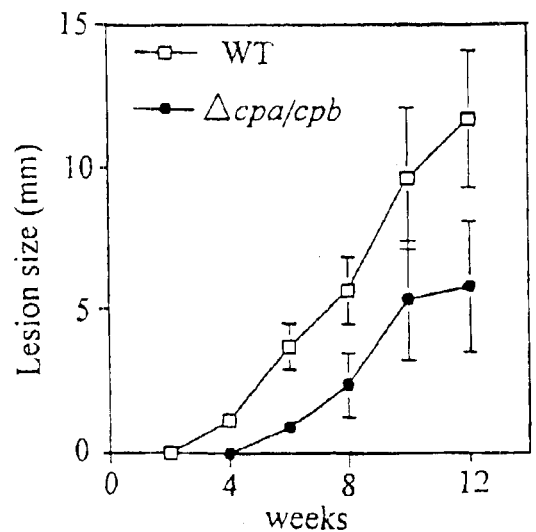
Figure 7C:
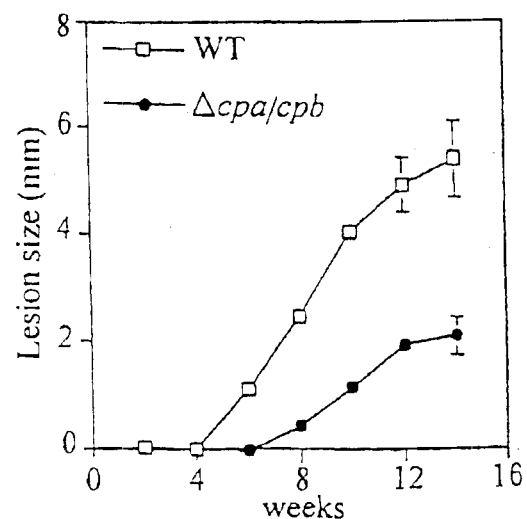

FIG. 4 shows IFN-γ production by cultured splenocytes removed from BALB/c mice 9 months post-infection with wild type (WT), Δcpa, Δcpb, or Δcpa/cpb stationary phase *L. mexicana* promastigotes. Cytokine analysis was performed on antigen (5 μg/ml)-stimulated (a) or Con A-stimulated (b) cultures. Non-stimulated cultures (0 μg/ml) were used as controls. Bars represent SEM;

FIG. 5a shows IL-2 and FIG. 5b IL-4 production by cultured splenocytes removed from BALB/c mice 6 months post-infection with wild type (WT) or Δcpa/cpb stationary phase promastigotes. Cytokine analysis was performed on antigen (5 Δg/ml)-stimulated or non-stimulated (0 μg/ml) cultures. Bars represent SEM. FIG. 5c shows IL-4 production by splenocytes from mice 9 months post-infection with wild type (WT) or Δcpb (N53) or Δcpb/cpa (DN) or Δcpa (H2B1) stationary phase promastigotes;

FIG. 6a shows IL-2, FIG. 6b IL-4 and FIG. 6c IFN-γ production by cultured splenocytes removed from C57BL/6 mice 6 months post infection with wild type (WT) or Δcpa/cpb stationary phase promastigotes. FIG. 6d shows IFN-γ production by cultured splenocytes removed from vaccinated CBA/Ca mice (Δcpa/cpb) or naive mice (WT) 8 weeks post-challenge with wild-type parasites. Cytokine analysis was performed on antigen (5 μg/ml) stimulated-or non-stimulated (0 μg/ml) cultures. IFN-γ production by Con A (5 μg/ml)-stimulated cultures are also included (FIG. 6c). Bars represent SEM;

FIG. 7 shows lesion growth as measured by diameter in BALB/c mice, (a,b) or C57BL/6 mice (c) non-vaccinated (○), or vaccinated with Δcpa/cpb stationary phase promastigotes (•) 2 months (FIG. 7a) or 4 months (FIG. 7b) before infection with wild type parasites. Bars represent SEM. Lesion growth was significantly slower until week 12 in the two month vaccinated group (<0.05) and until week 8 and at week 12 in the 4 month vaccinated group (<0.05). Three of the non-vaccinated mice in the latter experiment had to be sacrificed at 10 weeks post-infection and 3 at 12 weeks post-infection because of the excessive lesion growth. Consequently the lesion size data shown for the non-vaccinated mice from 10 weeks onwards is artificially low as they do not take into account the lesions of the sacrificed mice. With C57BL/6 (FIG. 7c), lesion growth-was significantly less throughout in vaccinated mice (•) compared with naive mice (○).

FIG. 8 shows the DNA sequence of the *Leishmania infantum* cpa gene (Seq. ID No. 1);

FIG. 9 shows the predicted protein sequence of *L. infantum* cpa (Seq. ID No. 2);

FIG. 10 shows nucleic acid sequence of the *L. infantum* cpb gene (Seq. ID No. 3); and FIG. 11 shows predicted protein sequence of the *L. infantum* cpb gene (Seq. ID No. 4).

MATERIALS AND METHODS

Parasites. Promastiaotes of *L. mexicana* (MNYC/BZ/62/M379) were grown in HOMEM medium, pH 7.5, containing 10% (v/v) heat inactivated foetal calf serum (HIFCS) at 25° C. as described in Mottram et al, 1992. The following antibiotics were added in combination, as appropriate, for maintenance of drug selectable markers in the cp-deficient mutants: phleomycin (Cayla, France) at 10 μg/ml, nourseothricin hydrosulphate (Hans-Knoll Institute, Thuringen, Germany) at 25 μg/ml puromycin (Sigma) at 10 μg/ml and hygromycin (Boehringer) at 50 μg/ml.

Mice. BALB/c, C57BL/6, CBA/Ca, 129Sv/Ev, C57BL/6 recombinant activating gene-deficient mice (RAG2–/–), were bred and maintained at the Universities of Glasgow and Strathclyde. Unless stated otherwise, groups of up to 20 female, 8–10 week old mice were infected subcutaneously in the shaven rump with $5 \times 10^6$ stationary phase promastigotes of wild type or cp-deficient *L. mexicana*. Groups of normally 5 but no less than 4 mice were used from each group for each sample point for each experiment. Lesion size was measured using a slide gauge micrometer. In the initial experiments undertaken at the University of Glasgow lesions volume was measured. Thereafter at the University of Strathclyde lesion diameters were measured and whole parasite burdens from excised disrupted lesions using a Neubauer haemocytometer were assessed.

Detection of *Leishmania*-specific antibodies by ELISA. Peripheral blood was obtained from infected animals by tail bleeding into heparinised capillary tubes. All plasma samples were stored at −20° C. prior to analysis for specific antibody content. *Leishmania*-specific IgG1 and IgG2a endpoint titres were measured by ELISA as previously described in Satoskar et al, 1995. Briefly, each well of an Immulon-1 microtitre plate (Dunatech Laboratories Ltd, Billingshurst, UK) was coated with 1 μg of leishmanial lysate antigen (freeze/thawed wild type promastigotes in phosphate buffered saline (PBS), pH 0.9) by overnight incubation at 4° C. Following incubation of serial dilutions of plasma samples for 1 h at 37° C., bound antibodies were detected by incubation with either rat anti-mouse IgG1 horseradish peroxidase conjugate or rat anti-mouse IgG2a horseradish peroxidase conjugate (Southern Biotechnology Associates, Birmingham, Ala., USA). Binding of conjugate was visualized with tetramethylbenzidine (0.06 mg/ml) in 0.1 M sodium acetate buffer, pH 5.5, containing 0.03% $H_2O_2$. The colour reaction was stopped by adding 10% (v/v) sulphuric acid and the absorbance measured at 450 nm. Results are expressed as end point dilutions where the end point is defined as the final plasma concentration which yielded an absorbance higher than a negative control plasma sample included in the assay. Comparisons between groups were made with a Mann Whitney U test.

Splenocyte responses. Spleens were aseptically removed at appropriate times post-infection, as detailed for individual experiments, and cell suspensions prepared by gently teasing apart the tissue in RPMI 1640 supplemented with 2 mM L-glutamine, 100 units/ml penicillin, 100 μg/ml streptomycin, 0.05 mM β-mercaptoethanol and 10% (v/v) HIFCS (Gibco, Paisley, UK). Following centrifugation at 200×g for 10 min at 4° C., cells were resuspended in 3 ml, Boyle's solution (0.17 M Tris-HCl, pH 7.2, 0.16 M ammonium chloride) at 37° C. for 3 min to deplete red blood cells. Spleen cell suspensions were then centrifuged at 200×g for 10 min at 4° C., resuspended, washed, and resuspended in 2 ml of complete RPMI 1640 medium (as above). Viable cells were enumerated by trypan blue exclusion and the suspensions adjusted to $5 \times 10^6$ cells/ml. 100 μl aliquots of the cell suspension were added to 96-well, flat-bottomed, tissue culture plates (Costar, Cambridge, Mass.) and 100 μl aliquots of concanavalin A (Con A, 5 μg/ml) or *L. mexicana* lysate antigen (5, 10 or 25 μg protein/ml) added as appropriate. Cultures were then incubated in 5% $CO^2$/95% air for 60 h at 37° C., whereupon cultures were pulsed with 0.25 μCi of [$^3$H]TdR (sp. act. 2 Ci/nmol) and incubated for a further 12 h. Supernatants were collected from parallel cultures at this time for quantification of cytokine production (see below). Pulsed cells were then harvested onto filter paper using a cell harvester (Skatron, Lier, Norway) and TdR uptake determined by liquid scintillation on a beta counter (Pharmacia LKB Biotech, Milton Keynes, UK).

IFN-γ, IL-2 and IL-4 assays. IFN-γ, IL-2 and IL-4 production by stimulated (by *Leishmania* antigen or Con A) and non-stimulated cells from mice infected with wild type or CP-deficient parasites were measured by capture ELISA. Briefly, the wells of Immunol-1 microtitre plates (Dynatech Laboratories Ltd, Billinghurst, UK) were coated with capture antibody at 2.0 μg/ml (IFN-γ R4-6A2; IL-2 JES6-1A1.2 Pharmingen, San Diego, Calif., USA; IL-4 llBll, Genzyme, Cambridge, UK) in PBS (pH 9.0) or carbonate buffer (0.05 M, pH 9.5) by overnight incubation at 4° C. Wells were then washed three times with PBS, pH 7.4/0.05% Tween-20 and blocked by incubation with 10% (v/v) FCS for 1 h at 37° C. The culture supernatants and appropriate recombinant standards (rIFN-γ, rIL-2, Pharmingen; rIL-4, Genzyme) were then added to individual wells. For standard curves, rIFN-γ (rIFN-γ(0–10 ng/ml), IL-2 (0–1350 pg/ml) and rIL-4 (0–1000 pg/ml) were used. Following incubations at 37° C. for 2 h, the wells were washed three times with PBS, pH 7.4/0.05% Tween-20 and then biotinylated rat anti-mouse IFN-γ (XMG1.2, Pharmingen; used at 1 μg/ml), biotinylated rat anti-mouse IL-2 (JES6-5H4, Pharmingen, used at 1 μg/ml) or goat polyclonal anti-IL-4 (Genzyme; used at 1 μg/ml) were added and incubated for 1 h at 37° C. For the detection of bound biotinylated rat antibody, 100 μl of streptavidin-alkaline phosphatase conjugate (diluted 1/1000, Pharmingen) was added to each well for 45 min at 3720 C. and, following further washing, binding was visualized with substrate consisting of p-nitrophenyl phosphate (1 mg/ml; Sigma, UK) in glycine buffer (0.1 M, pH 10.4). The absorbance was subsequently measured at 405 nm on a Titertek Multiscan Plate Reader. For detection of bound biotinylated goat antibody, 100 μl of streptavidin-horseradish peroxidase conjugate (diluted 1/500, Genzyme) was added to each well for 30 min at 37° C. and following further washing was incubated with tetramethylbenzidine as described above. Cytokine concentrations in the cell cultures were determined from the standard curve (regression coefficient, r=0.990 or better) All assays were carried out in triplicate. Comparisons between groups were made using the Student's t test. P values of <0.05 were considered significant.

Vaccine studies. Three mouse strains (BALB/c, CBA/Ca and C57BL/6) that develop non-healing lesions when infected with *L. mexicana* and have been used previously for vaccine studies were examined. The protocols for each mouse strain were modified to reflect their response to CP-deficient mutants. Two and 4 months post-inoculation sub-cutaneously in the flank with $5 \times 10^6$ Δcpa/cpb stationary phase promastigotes, BALB/c mice were infected sub-cutaneously into the shaven rump with $5 \times 10^6$ wild type parasites and disease progression was compared with non-vaccinated mice. CBA/Ca and C57BL/6 mice were vaccinated with Δcpa/cpb (sub-cutaneous inoculation of $10^7$ stationary phase promastigotes) and challenged 6 weeks later with $2 \times 10^5$ wild type *L. mexicana*. Lesion growth was monitored and compared with non-vaccinated control animals.

Example 1

Generation of *L. mexicana* Cysteine Proteinase Single and Double Null Mutants.

*L. mexicana* cysteine proteinase single (Δcpa or Δcpb) and double null mutants (Δcpa/cpb) which contain defective cpa and/or cpb genes, were prepared according to the procedure described in Mottram et al 1996.

Example 2

Figure 1:
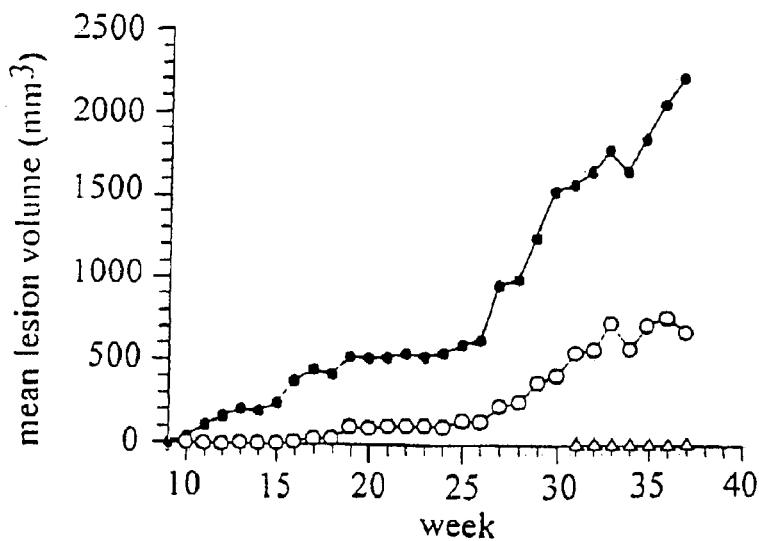

Infectivity of Wild Type, Single Null and Double Null *L. Mexicana* Cysteine Proteinase Deficient Mutants After sub-intaneous inoculation with $5 \times 10^6$ promastigotes suspended in phosphate buffered saline, BALB/c mice were observed for lesion formation (see FIG. 1a).

It was observed that both the wild-type and single null mutants resulted in the generation of lesions, although notably the single null mutant produces lesions which grow at significantly slower rates than wild-type parasites and are about 100-fold smaller. The lesions resulting from infection with Δcpb were slow to appear (first appearance at week 31) and very small (mean lesion volume at week 37 was 3.5 $mm^3$). No lesions were observed in animals which were inoculated with the cpa/cpb double null mutant.

Figure 2:
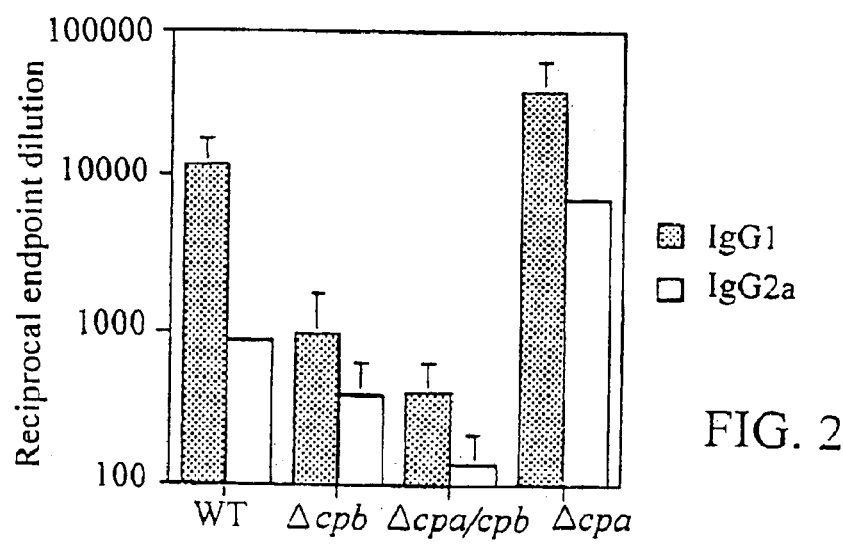
FIG. 2 shows analysis of plasma IgG1 and IgG2a levels in BALB/c mice 6 months after infection with wild type (WT), Δcpa, Δcpb, or Δcpa/cpb stationary phase *L. mexicana* promastigotes. Values represent mean end point dilutions±SEM.

Example 3
Immune Response to *L. mexicana* Cysteine Proteinase Single and Double Null Mutants Antibody response generated following infection with wild type or CP-deficient *L. mexicana*. Plasma levels of *Leishmania*-specific IgG1 and IgG2a were determined 6 months post-infection (FIG. 2). Animals infected with wild type *L. mexicana* had pronounced *Leishmania*-specific antibody levels, primarily of the IgG1 subclass. Mice infected with Δcpa also had large antibody titres, primarily of the IgG1 subclass but with significantly higher IgG2a titres than those following infection with wild type *L. mexicana* ($p<0.01$). Mice infected with Δcpb had significantly less IgG1 antibody than animals infected with wild type *L. mexicana* ($p<0.01$), and there was a distinct and significant increase in the IgG2a/IgG1 ratio. Mice infected with Δcpa/cpb had very little detectable *Leishmania*-specific antibody.

Figure 3:
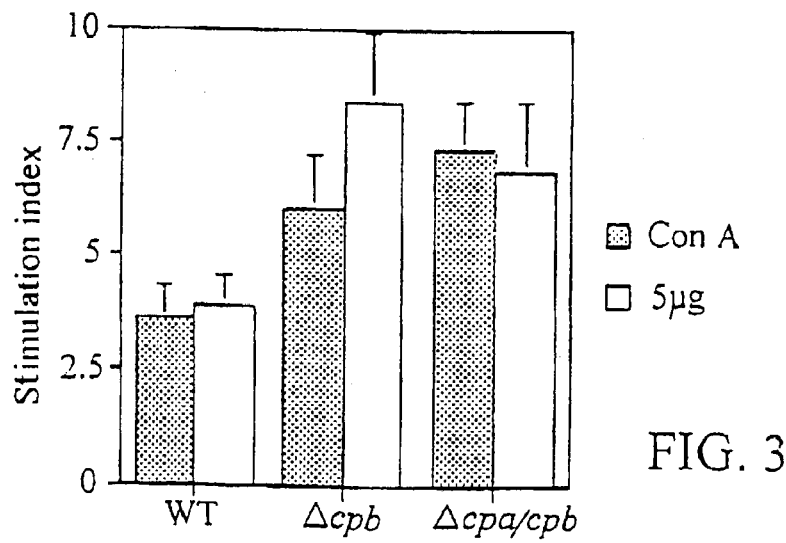
FIG. 3 shows Con A (5 μg/ml) or *L. mexicana* lysate (5 μg/ml) induced splenocyte proliferation responses in *L. mexicana* wild type (WT)-infected or Δcpb-, Δcpa/cpb-infected BALB/c mice 6 months post-infection. Data represented as mean stimulation index±SEM.
Figure 4A:
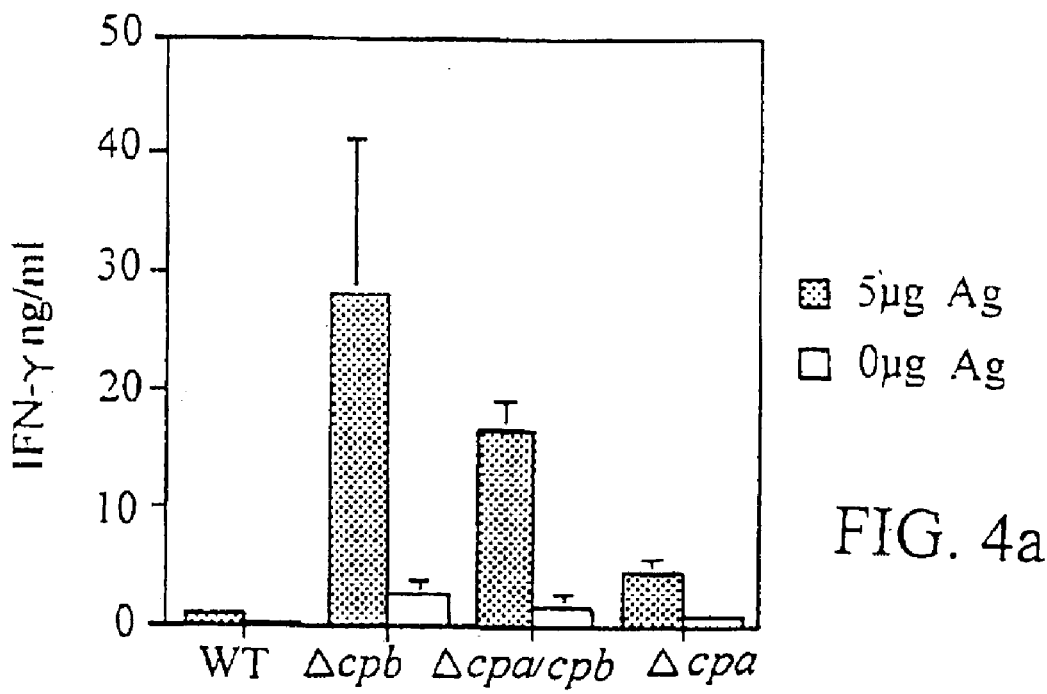
Figure 4B:
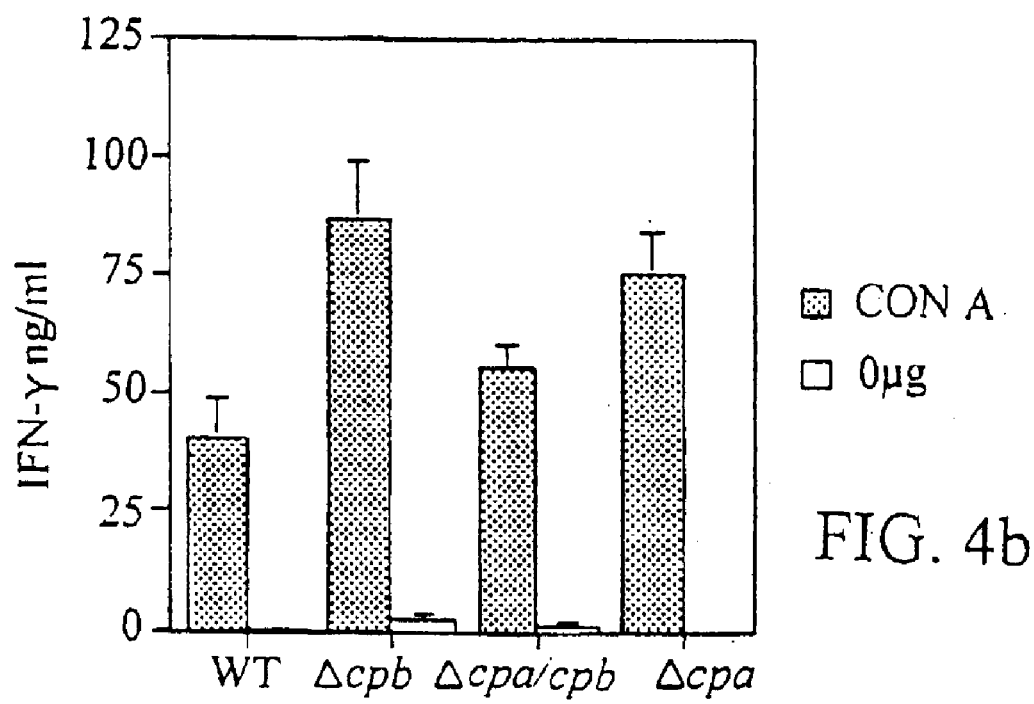

In vitro splenocyte proliferative responses following infection with wild type or CP-deficient *L. mexicana*. Both wild type and CP-deficient mutant infected mice were able to mount antigen-specific and Con A-induced proliferative responses at all time points examined (2, 4, 6 and 9 months) in all experiments. From 2 months onwards the antigen-specific and from 6 months onwards the Con A-induced proliferative responses were significantly greater in Δcpa/cpb ($p<0.05$ for Con A and antigen) and Δcpb ($p<0.05$ for Con A and antigen) inoculated mice than those mice inoculated with wild type parasites (FIG. 3). IFN-γ production by stimulated splenocytes from infected mice. IFN-γ production from splenocytes isolated from BALB/c mice 9 months post-infection and stimulated with parasite antigen (5 μg protein/ml) or Con A are shown in FIGS. 4a and b. Similar results were found for different amounts of antigen used and at earlier time post-infection (not shown) Antigen stimulation resulted in significantly increased IFN-γ production in comparison with background levels ($p<0.05$) by all splenocyte cultures (FIG. 4a). However, production was significantly greater by antigen-stimulated splenocytes from animals infected with CP-deficient mutants than with wild type *L. mexicana* (Δcpa and Δcpb, $p<0.05$; Δcpa/cpb, $p<0.005$). Moreover, antigen-induced IFN-γ production was significantly greater from splenocytes isolated from mice infected with Δcpb ($p<0.05$) and Δcpa/cpb ($p<0.01$) than from splenocytes isolated from Δcpa-infected mice. Con A stimulation increased IFN-γ production to significantly greater levels than background in all splenocyte cultures. Under these conditions, splenocytes derived from mice infected with Δcpa ($p<0.05$) and Δcpb ($p<0.02$) but not Δcpa/cpb produced significantly more IFN-γ than splenocytes derived from mice with wild type infections (FIG. 4b).

IL-2 and IL-4 production by stimulated splenocytes from infected mice. Subsequent studies concentrated on comparing the developing immune response in mice infected with Δcpa/cpb and wild type parasites. In addition to confirming differences in splenocyte IFN-γ production, IL-2, IL-4, IL-5, IL-10 and IL-12 production was measured. No differences in splenocyte IL-5, IL-10 and IL-12 production were observed between Δcpa/cpb and wild type parasite infected mice, however profound differences in IL-2 and IL-4 production were observed at 2, and in particular, 4 and 6 months post-infection (FIGS. 5a and b). While splenocytes from animals infected with wild type parasites failed to produce a significant antigen-induced increase in IL-2 production, those infected with Δcpa/cpb produced, following stimulation with antigen, IL-2 significantly over background ($p<0.01$). Antigen-stimulated splenocyte IL-4 production (at 6 months post infection) was significant over background for both Δcpa/cpb ($p<0.001$) and wild type infected ($p<0.001$) animals. However, the increase in splenocyte IL-4 production was significantly greater in wild type infected animals than Δcpa/cpb infections ($p<0.001$).

Infectivity of CP-deficient mutants for other mouse strains. Δcpa/cpb parasites failed to induce lesions growth not only in C57BL/6, CBA/Ca and 129Sv/Ev mice but also in RAG2-deficient C57BL/6 mice up to 6 months post infection (results not shown). Small lesions were, however, induced in C57BL/6 and RAG2−/− mice by inoculation with Δcpb (results not shown). All animals infected with wild type parasites developed large non-healing lesions. The immunological responses generated by wild type parasites or CP-deficient mutants in the wild type mouse strains were examined and were similar to those observed in BALB/c mice. In C57BL/6 mice, antigen-induced splenocyte cytokine production in animals inoculated 6 months previously with Δcpa/cpb consisted entirely of IFN-γ ($p<0.01$) and IL-2 ($p<0.05$) with virtually no IL-4 produced above background levels (FIGS. 6a, b and c). However, antigen-stimulated splenocytes from animals inoculated with wild type parasites produced not only significant levels of IFN-γ ($p<0.05$) but also IL-4 ($p<0.01$) with little or no IL-2 above background levels. Although IFN-γ levels following antigen stimulation were similar in both groups, the increase in splenocyte IFN-γ production in antigen-stimulated Δcpa/cpb-inoculated animals ($5.79\pm1.53$ pg/ml) over background (and $0.11\pm0.05$ pg/ml) was 10-fold greater than that produced over background by splenocytes from wild type-infected mice ($6.03\pm3.25$ and $0.99\pm0.43$ pg/ml, respectively). Con A-induced splenocyte IFN-γ production was also significantly greater ($p<0.05$) in mice inoculated with Δcpa/cpb than in mice inoculated with wild type parasites.

Vaccine potential of CP-deficient mutants. BALB/c mice vaccinated with the mutant parasites 2 or 4 months before infection with wild type parasites produced slower growing lesions (FIGS. 7a and b) which contained significantly fewer parasites than similarly infected non-vaccinated mice. At week 8 post-infection with wild type *L. mexicana*, the parasite burdens in mice vaccinated 2 months and 4 months previously with Δcpa/cpb were significantly less than non-vaccinated mice (vaccinated, two months $2.7\times10^6\pm5.4\times10^5$ and 4 months $1.6\times10^6\pm3.2\times10^5$; non-vaccinated, $6.2\times10^7\pm2.27\times10^7$ and $8.4\times10^7\pm2.4\times10^7$), ($p<0.002$ and $p<0.001$ respectively). Whereas, all non-vaccinated and the vast majority of vaccinated mice went on to develop non-healing lesions, two of the 10 mice infected 4 months after vaccination failed to develop lesions up to 12 weeks post-challenge.

CBA/Ca mice were also used in a vaccine study as they have been shown to be more amenable to vaccination than BALB/c mice and also fail to develop lesions following challenge with Δcpb All non-vaccinated mice developed non-healing cutaneous lesions following infection with wild type *L. mexicana* promastigotes. However, only 1 of 4 mice vaccinated with Δcpb and only 1 of 5 mice vaccinated with Δcpa/cpb had developed lesions 5 months after challenge (Table 1).

TABLE 1

Incidence of cutaneous lesion development in non vaccinated or CP null mutant vaccinated CBA/Ca mice infected with $2 \times 10^5$ L. mexicana wild type promastigotes.

| Vaccine | | No. Mice with/without lesions (week 20) |
|---|---|---|
| Group 1 | — | 5/0 |
| Group 2 | N53* | 1/3 |
| Group 3 | DN* | 1/4 |

*Mice were vaccinated subcutaneously with $10^7$ stationary phase promastigotes of Δcpb (N53) single null mutant or Δcpa/cpb (DN) double null mutants 6 weeks prior to challenge infection.

Efficacy of the cpb/cpa Double Null Mutant as a Vaccine
1. Using a similar protocol as for BALB/c mice, protection in C57BL6 mice was very significant (see FIG. 7c). Key: □, unvaccinated mice; •, vaccinated mice.
2. Using a similar protocol as for BALB/c mice, protection in CBA/Ca mice at 13 weeks post-challenge was complete. There were no lesions in any of the 10 vaccinated mice, whereas with the unvaccinated mice lesions first appeared 6–8 weeks post-challenge in 8 of the group of 10.
3. Splenocytes removed 8 weeks post-challenge from CBA/Ca mice vaccinated with the cpb/cpa double null mutant produced significantly more IFN-gamma than did splenocytes from unvaccinated mice (see FIG. 6d). This showed that challenge with wild type parasites did not cause reversion of vaccinated animals to a Th2 response.

Example 4
Expression of Active and Inactive Forms of Recombinant CPB

Details described below are for the generation, expression and purification of active CPB. However, the same protocol may essentially be followed for the production of inactive CPB.

Cloning cpbg2.8 into pQE-30

PCR Amplification of *Leishmania Mexicana* cpb2.8

A PCR product was amplified from the lmcpb2.8 gene (Mottram et al., 1996, Proc. Natl. Acad. Sci. USA, EMBL data base number Z49962) using primers JH9601 and JH9602:

```
Primer JH9601  GGATCCGCCTGCGCACCTGCGCGCGCGA

Primer JH9602  AAGCTTCTACCGCACATGCGCGGACACGG
```

| PCR Conditions: | | |
|---|---|---|
| 94° C., | 4 mins | x1 |
| 94° C., | 30 secs | |
| 55° C., | 30 secs | x15 |
| 72° C., | 2 mins | |
| 72° C., | 7 mins | x1 |

20 μl reactions using 0.5 μl (1 unit) of VENT Polymerase (New England Biolabs) with 11.1×PCR mix. After the PCR reaction was complete, A overhangs were added by incubating with Taq Polymerase at 72° C. for 10 minutes before DNA was phenol/chloroform extracted and ethanol precipitated.

Cloning of cpbg2.8

The cpbg2.8 PCR product was cloned into the pTAG vector (R&D Systems). It was then excised from pTAG with BamHI and HindIII and cloned into the pQE-30 vector (Qiagen), using the same restriction enzymes, to give plasmid clone pGL180. pGL180 was transformed into M15 [pREP4] *Esherichia coli* for expression studies.

Expression of Recombinant CPB2.8

A single colony of the *E. coli* M15pREP4 expression strain transformed with the pQE-30 construct was inoculated into 8 ml of LB broth supplemented with ampicillin (100 μg.ml$^{-1}$) and kanamycin (25 μg.ml$^{-1}$) and grown at 37° C. This culture was used to inoculate 400 ml of LB/Anp/Kan broth and the culture grown until an $OD_{600}$ of 0.7 was obtained. The expression of CPB2.8 was induced by the addition of IPTG to a final concentration of 1 mM. After 3 hours, the bacterial cells were pelleted by centrifugation at 4000 g for 10 min.

Isolation of Active, Recombinant CPB2.8 from the Soluble Fraction

The bacterial pellet was resuspended in 10 ml of 50 mM Tris/HCl buffer, pH 8 containing 5 mM EDTA and 5%(w/v) sucrose. The suspension was subjected to two rounds of freeze-thaw and six 30 second bursts on a sonicator at 4° C. The bacterial lysate was centrifuged at 6000 g for 10 min to pellet insoluble material and leave a supernatant fraction containing recombinant enzyme. This soluble fraction was dialysed for 3 hours against 400 volumes of 0.1 M Tris/HCl buffer, pH 8, 0.5 M KCl, 1 mM β-mercaptoethanol (buffer A). The sample was filtered through a 0.22 μm filter and loaded directly at 0.2 ml.min$^{-1}$ onto a Ni-agarose (Qiagen) column pre-equilibrated in buffer A. The chromatography was effected with a stepped gradient of 0–1 mM imidazole in 0.1 M Tris/HCl buffer, pH 8, 0.5 M KCl, 1 mM β-mercaptoethanol at a flow rate of 1 ml.min$^{-1}$. Contaminating proteins eluted from the column in 10 ml of buffer A. The recombinant CPB2.8 enzyme was eluted with 10–20 mM imidazole in buffer A. Purity of the enzyme was assessed using silver stained SDS-PAGE. The yield from 200 ml of culture was approximately 1–2 mg of CPB2.8 enzyme.

Isolation of Active, Recombinant CPB2.8 from the Inclusion Bodies

Following bacterial cell lysis as described above, the pelleted inclusion bodies were washed (that is, resuspended and then subsequently pelleted again via 6000 g for 10 min) once in 10 ml of 50 mM Tris/HCl buffer, pH 8 containing 5 mM EDTA, 0.1% Triton X100, twice in 10 ml of 50 mM Tris/HCl buffer, pH 8 containing 5 mM EDTA, 2 M urea, and then finally once in 10 ml of distilled, deionised water. The washed pellet was solubilised at 37° C. with vigorous shaking in 10 ml of 0.1 M Tris/HCl buffer, pH 8 containing 8 M urea, 10 mM DTT. The solubilised CPB2.8 was diluted to a final protein concentration of 0.01–0.5 mg.ml$^{-1}$ in 0.1 M Tris/HCl buffer, pH 8 containing 5 mM EDTA, 8 M urea. The CPB2.8 enzyme was then allowed to refold to native conformation by the removal of the chaotroph by dialysis for 15 hours against 100 volume of 0.1M Tris/HCl buffer, pH 7 containing 5 mM EDTA, 5 mM cysteine. The reducing agent was then removed by dialysis for 2 hours against 100 volume of the same buffer minus cysteine. The active enzyme resulting from this procedure was then purified by ion exchange chromatography.

Purification of Active, Recombinant CPB2.8

The refolded CPB2.8 was filtered through a 0.22 μm filter and loaded immediately at 1 ml.min$^{-1}$ onto a 1 ml Mono Q column pre-equilibrated in 20 mM Tris/HCl, pH 7, 0.01%

Triton X100 (buffer B). The chromatography was developed at a flow rate of 1 ml.min$^{-1}$ with a stepped gradient of 0–1 M NaCl in buffer B. Pro-enzyme eluted over 200–600 mM NaCl and mature enzyme with 400–600 mM NaCl. Samples were dialysed against 20 mM Tris/HCl, pH 7, 0.01% Triton X-100 to remove salt, and frozen until use. Purity was assessed using silver stained SDS-PAGE. Yield of active, pure CPB2.8 was 4–5 mg from 200 ml of culture.

Example 5

Production of Recombinant Proteins of Mutated cpb and Expression of Mutated cpb in Null Mutant Parasites as Vaccine Candidates The genes encoding different copies of CPB were mutated in a number of ways so that variants of the protein could be generated as candidate vaccines both within the attenuated *leishmania* themselves and as recombinant proteins.

Constructs used for Transfections Resulting in Episomal Expression of CPB Isoenzymes The pX episomal shuttle vector (LeBowitz et al., 1990) was utilised for transfection of either the *L. mexicana* Δcpb null mutant or Δcpa/cpb double null mutant. All genes were ligated to the XmaI site of pX following the creation of blunt ends as required The cDNA (Souza et al., 1992) and cpb2.8 (Mottram et al., 1996) were subcloned from pBluescript as a 2.2-kb XbaI-XhoI fragment and a 2.0-kb EcoRV fragment, respectively. Mutations were incorporated into the pBluescript constructs of these genes using the QuikChange Site-Directed mutagenesis kit (Stratagene) and verified by sequence analysis prior to subcloning into pX as above. Primers used were as follows (only the sense strand primer is shown and the mutated sites are underlined):

```
a)  CPB2.8 mut ASM,
    GGTGCGTGCGGGTCGGCTGGGCGTTCTCGG b)  CPB2.8 mut glycos,
    GCCCGAGTGCTCGAGCAGCAGTGAGCTCG c)  cDNA mut 18,
    GACGCCGGTGAAGAATCAGGGTGCGTG d)  cDNA mut 84,
    CGAACGGGCACCTGTACACGGAGGACAGC e)  cDNAmutx3,
    GCTGCGATGACATGAACGATGGTTGCGACGGCGGGCTGATGC
```

Mutant (a) Residue 25 of cpbg2.8 from a cysteine to a glycine. This mutation removes the active site cysteine.

(b) Residue 103 of cpbg2.8 from an asparagine to a serine. This mutation removes the glycosylation site.

(c) Residue 19 of cpb cDNA from an aspartic acid to an asparagine, alters activity of cpb cDNA.

(d) Residue 84 of cpb cDNA from a histidine to a tyrosine. Alters activity of cpb cDNA.

(e) Residues 60, 61 and 64 of cpb cDNA from aspartic acid (60), asparagine (61) and serine (64) to asparagine, aspartic acid and aspartic acid respectively. Alters activity of cpb cDNA.

All sequencing was performed with an ABI 373 DNA sequencer (Perkin-Elmer) and analysed using the Wisconsin GCG package Constructs Used for Transfections Resulting in Expression of cpb Isoenzymes from Genes Integrated into the Genome As an alternative to episomal expression, cpb genes (both wild type and mutated) were integrated into the *L. mexicana* cysteine proteinase null mutants by homologous recombination, utilizing a construct containing the unique 5' and 3' sequences flanking the cpb array (Mottram et al., 1996).

Transfection of *L. mexicana*

Transfection of *L. mexicana* promastigotes was as described previously (Souza et al., 1994; Mottram et al., 1996). Briefly, pX-based constructs were prepared using Qiagen Tip100 columns as described by the manufacturer. Transfection utilised 10 $\mu$g of DNA and $4\times10^7$ late-log phase promastigotes. Following electroporation, cells were allowed to recover in 10 ml HOMEM for 24 h at 25 C and then transfectants were selected for by transfer of cells into HOMFM containing 25 $\mu$g/ml G418.

The lines expressing the mutated cpbs and the mutated, inactive CPBs themselves were used to vaccinate animals.

Example 6

Isolation of *Leishmania Infantum* cpa and cpb Genes

In Mediterranean countries, *L. infantum* is responsible for both visceral and cutaneous leishmaniasis with the dog serving as the principal reservoir. In Spain, for example, there is a prevalence of 0.3 Visceral Leishmaniasis cases per 100,000 inhabitants and it is calculated that between 3% and 5% of all Spanish dogs are seropositive.

The *L. infantum* cpa and cpb genes were isolated by screening a *L. infantum* genomic library (Soto et al., 1993) with *L. mexicana* cpa (Mottram et al., 1992) and cpb (Souza et al., 1992)-specific gene probes. The genomic library was prepared in the EMBL3 lambda vector from total DNA partially digested with Sau3A1 from a *L. infantum* strain from a case of human Visceral Leishmaniasis (reference strain, MHOM/FR/78/LEM-75). 3 lambda clones were isolated for *L. infantum* cpa and 4 lambda clones were isolated for *L. infantum* cpb.

The complete open reading frame of the *L. infantum* cpa gene, together with 5' and 3' flanking sequence, was subcloned on a 3.2 kb PstI fragment into pBluescript vector for sequencing (FIG. 8). The *L. infantum* cpa gene has 89% nucleotide sequence identity with the *L. mexicana* cpa gene (Mottram et al., 1992) and 92% identity with the *L. chagasi* cpa gene (Omara-Opyene and Gedamu, 1997). The predicted *L. infantum* protein (FIG. 9) has 86% amino acid sequence identity with *L. mexicana* CPA and 89% identity with the *L. chagasi* CPA (Omara-Opyene and Gedamu, 1997). Outwith the open reading frame of the cpa genes, there is sequence variation in the 5' and 3' flanks that will allow the design of specific gene targeting fragments for deletion of the *L. infantum* cpa gene.

A PCR approach was used to amplify the complete ORF of a cpb gene from one of the *L. infantum* lambda clones containing cpb. Sense and antisense primers were designed based on the *L. mexicana* and *L. chagasi* cysteine proteinase sequences. The sequences of the two primers for cpb were:

```
sense primer     5' GTGCGAGCTGTGGCCTCTGCGT 3' and
(CPBM1)

antisense primer 5' GGCGCGCGCGCACCCAAGG 3'.
(CPBM2),
```

PCR reactions were carried out using DNA from lambda as template, 5% DMSO and Taq and KlenTaq LA polymerase (Sigma). Conditions used in PCR were 94° 5', 15 cycles (94° 1', 45° 2', 72° 2') and final extension 72° 5'. The temperature for the extension was 68° C. when the PCR used KlenTaq LA polymerase. 1.7 kb cpb PCR products were cloned into the pGEM-T vector. Sequence from the *L. infantum* cpb PCR products showed >85% identity with the *L. mexicana* cpb gene (FIG. 10).

REFERENCES

Afonso, L. C. C. & Scott, P. (1993). Immune responses associates with suspectibility of C57BL10 mice to *Leishmania amazonensis*. Infect. Imnun. 61, 2952–2959.

Alexander, J & Russell, D. G. (1992). The interaction of *Leishmania* species with macrophages. Adv. Parasitol. 31, 175–254.

Bogdan, C., Geesner, A, Solbach, W. & Rollinghof, M. (1996) Invasion, control and persistence of *Leishmania* parasites. Curr. Opinion Immunol. 8, 517–525.

Barrett, A. J. and Rawlings, N. D. (1996) Families and clans of cysteine peptidases. Perspect. Drug Disc. Design 6, 1–11.

Bart, C., Coombs, G. H., & Mottram, J. C. (1995). Isolation of lmcpc, a gene encoding a *Leishmania mexicana* cathepsin B-like cysteine proteinase. Mol. Biochem. Parasitol. 73, 271–274.

Bray, R. S. (1982) The zoonotic potential, of reservoirs of leishmaniasis in the Old World. Ecol. Disease 1, 257–267.

Coombs, G. H. & Mottram, J. C. (1997). Proteinases of trypanosomes and *Leishmania*. In trypanosomiasis and leishmaniasis: Biology and control. G. Hide. G C Mottram, G H Coombs and P H Holmes, eds. (Oxford, UK: CAB International). Pp 177–197.

Dye, C., Killick-Kendrick, R., Vitutia M. M., Walton, R., Killick-Kendrick, M., Harith, A. E. Guy., M. W., Canavate, M C. & Hasibeder, G (1992) Epidemiology of canine leishmaniasis: prevalance, incidence and basic reproduction number calculated from a cross sectional serological survey on the island of Gozo, Malta. Parasitology 105, 35–41.

Finkeleman, F. D., Holmes, J., Katona, I. M., Urban J. F., Beckman, M. P. Park, L. S., Schooley, K. A., Coffman, R. L., Mossman, T R., & Paul, W E. (1990). Lymphokine control of in vivo immunoglobulin isotype selection. Ann. Rev. Immunol. 8, 303–333.

Kaye, P. M., Curry, A. J., & Blackwell, J. M. (1991). Different production of Th1-and Th2-derived cytokines does not determine the genetically controlled or vaccine induced rate of cure in murine visceral leishmaniasis. J. Immuol. 146, 1763–2770.

Kreig A. M. (1996) Trends in Microbiol. 4 pp. 73–77.

Lebowitz, J. H. (1994) Transfection experiments with *leishmania*. Meth Cell Biol. 45, 65–78.

LeBowitz, J. H., Coburn, C. M., McMahon-Pratt, D., and Beverley, S. M. (1190). Development of a stable *Leishmania* expression vector and application to the study of parasite surface-antigen genes. Proc. Natl. Acad. Sci. USA 87, 9736–9740.

Liew, F. Y. & O'Donnel, C A (1993). Immunology of leishmanisis. Adv. Parasitol. 32, 161–258.

Mottram, J. C., Robertson, C. D., Coombs, G. H & Barry, J D (1992). A developmentally regulated cysteine proteinase gene of *Leishmania mexicana*. Mol. Microbiol. 6, 1925–1932.

Mottram J. C., Souza, A. E., Hutchinson, J. E., Carter, R, Frame M. J. & Coombs, G. H. (1996). Evidence from disruption of the lmcpb gene array of *Leishmania mexicana* that cysteine proteinases are virulence factors. Proc Natl. Acad. Sci. US 93, 6008-6013.

Noben-Trauth, N., Kropf, P & Muller, I (1996). Suspceptibility to *Leishmania* major infection in interleukin-4-deficient mice. Science 271, 987–990.

Omara-Opyene, A. L. and Gedamu, L. (1997). Molecular cloning, characterization and overexpression of two distinct cysteine protease cDNAs from *Leishmania donovani* chagasi. Mol. Biochem. Parasitol. 90, 247–267.

Roberts, M., Alexander, J. & Blackwell, J. M. (1989). Influence of Lsh, H-2 and an H-11 linked gene on visceralization and metastasis associated with *Leishmania mexicana* infection in mice. Infect Immun. 57, 875–881.

Roberts, M., Alexander J. & Blackwell J M. (1990). Genetic analysis of *Leishmania mexicana* infection in mice: single gene (scl-2) controlled predisposition to cutaneous lesion development. J. Imunogen. 17, 89–100.

Robertson, C. D, Coombs, G. H., North. M. J & Mottram, J. C. (1996). Parasite cysteine proteinases Perspect. Drug Disc. Design 6, 99–118.

Sato Y., et al. Immunostimultary DNA sequences necessary for effective intradermal gene immunization. Science, 1996; 273: 352–354).

Satoskar, A. & Alexander, J, (1995). Sex mediated suspectibility and differential TNF-$\alpha$ and IFN-$\delta$ mRNA expression in DBA/2 mice infected with *Leishmania mexicana*. Immunology 84, 1–4.

Satoskar, A., Bluethmann, H & Alexander, J. (1995). Disruption of the murine interleukin-4 gene inhibits disease progression during *Leishmania mexicana* infection but does not increase control of *L. donovani* infection. Infect. Immun. 63, 4894–4899.

Soto, M., Requena, J. M., Garcia, M., Gomez, L. C., Navarrete, I., and Alonso, C. (1993). Genomic organization and expression of two independent gene arrays coding for two antigenic acidic ribosomal proteins of *Leishmania*. J. Biol. Chem. 268, 21835–21843.

Souza, A. E., Bates P. A., Coombs G. H. & Mottram J C (1994). Null mutants for the impca cysteine proteinase gene in *Leishmania mexicana*. Mol Biochem. Parasitol. 63, 213–220.

Souza, A. E., Waugh, S., Coombs, G. H., & Mottram, J. C. (1992). Characterization of a multicopy gene for a major stage-specific cysteine proteinase of *Leishmania mexicana*. FEBS Lett. 311, 124–127.

Titus, R. G., Gueriros-Filho, F. J., DeFreitas, LAR., and Beverely, S M. (1995) Development of a safe line *Leishmania* vaccine line by gene replacement. Proc. Natt. Acad. Scie. USA 92, 10267–10271.

What is claimed is:

1. A vaccine formulation comprising a mutant *Leishmania infantum*, said mutant *Leishmania infantum* comprising at least one defective cysteine proteinase gene, such that the mutant *Leishmania infantum* is substantially incapable of expressing a functionally active form of said at least one cysteine proteinase.

2. A vaccine formulation according to claim 1 wherein the mutant *Leishmania infantum* comprises two or more defective cysteine proteinases.

3. A vaccine formulation according to claim 1 wherein the mutant *L. infantum* comprises at least one defective proteinase gene selected from the group consisting of cpa and cpb.

4. A vaccine formulation according to claim 3 wherein the at least one *L. infantum* defective proteinase gene is selected from the group consisting of cpa that has the sequence shown in FIG. 8 and cpb that has the sequence as shown in FIG. 10.

5. A vaccine formulation according to claim 1 wherein the at least one defective cysteine proteinase gene has been modified by a deletion, insertion, substitution or rearrangement such that said at least one cysteine proteinase is substantially incapable of expressing a functionally competent cysteine proteinase.

6. A vaccine formulation according to claim 5 wherein said cysteine proteinase gene has been modified by deletion of all or a portion of said cysteine proteinase gene.

7. A vaccine formulation according to claim 6 wherein a gene or gene fragment capable of expressing a polypeptide selected from the group consisting of polypeptides which augment an immune response and marker polypeptides is inserted into a gap generated by deletion of all or the portion of said cysteine proteinase gene.

8. A vaccine formulation according to claim 7 wherein the polypeptide is a cytokine.

9. A vaccine formulation according to claim 7 wherein at least one copy of said cysteine proteinase gene has been modified such that a substantially inactive form of a cysteine proteinase polypeptide is expressed.

10. A vaccine formulation according to claim 1 wherein the mutant *Leishmania* is a drug resistant marker-free mutant.

11. A vaccine formulation according to claim 1 that elicits a cellular immune response when administered to a subject.

12. A vaccine formulaLion according to claim 11 wherein the cellular immune response is a Th1 cell response.

13. A vaccine formulation according to claim 1 further comprising an adjuvant and/or cytokine.

14. A vaccine formulation according to claim 1 further comprising at least one disfunctional cysteine proteinase, wherein said disfunctional cysteine proteinase is substantially enzymatically inactive, but which is antigenic or immunogenic.

15. A method of vaccinating a subject against *Leishmania* said method comprising administering to the subject an effective, non-toxic amount of a vaccine formulation according to claim 1.

16. A method according to claim 15 wherein the method comprises parenteral administration.

* * * * *

SEQUENCE LISTING

<160> NUMBER OF SEQ ID NOS: 13

<210> SEQ ID NO 1
<211> LENGTH: 1065
<212> TYPE: DNA
<213> ORGANISM: Leishmania infantum
<220> FEATURE:
<221> NAME/KEY: CDS
<222> LOCATION: (1)..(1065)

<400> SEQUENCE: 1

-continued

```
atg gcg cgc cgc aac tgc ttt ttg ttt gcg ata gtg gtg act atc ctg      48
Met Ala Arg Arg Asn Cys Phe Leu Phe Ala Ile Val Val Thr Ile Leu
1               5                   10                  15 ttc gtg gtg tgc tac ggt tcc gct ctc atc gcc cag aca cct ctc ggt      96
Phe Val Val Cys Tyr Gly Ser Ala Leu Ile Ala Gln Thr Pro Leu Gly
                20                  25                  30 gtc gac aac ttc att gcc tca gcg cat tac gga cgc ttt aag aag cac     144
Val Asp Asn Phe Ile Ala Ser Ala His Tyr Gly Arg Phe Lys Lys His
            35                  40                  45 cac ggc aag gcc ttc ggc gag gac gcc gag gag ggt cgc cgc ttc aat     192
His Gly Lys Ala Phe Gly Glu Asp Ala Glu Glu Gly Arg Arg Phe Asn
        50                  55                  60 gcc ttc aag cag aac atg cag aca gcc tac ttc ctc aac gcg cac aac     240
Ala Phe Lys Gln Asn Met Gln Thr Ala Tyr Phe Leu Asn Ala His Asn
65                  70                  75                  80 cca cac gcg cac tac gac gtg tcc ggc aag ttc gca gac ctc acc ccc     288
Pro His Ala His Tyr Asp Val Ser Gly Lys Phe Ala Asp Leu Thr Pro
                85                  90                  95 cag gag ttc gcc aag ctg tac cta aac ccc aac tac tac gcg cgc cac     336
Gln Glu Phe Ala Lys Leu Tyr Leu Asn Pro Asn Tyr Tyr Ala Arg His
            100                 105                 110 ggc aag gat tac aag gag cac gtg cac gtc gac gac agc gtc cgc agt     384
Gly Lys Asp Tyr Lys Glu His Val His Val Asp Asp Ser Val Arg Ser
        115                 120                 125 ggt gtg atg tcg ttg gac tgg cgt gag aag ggt gcc gtg aca ccg gtg     432
Gly Val Met Ser Leu Asp Trp Arg Glu Lys Gly Ala Val Thr Pro Val
130                 135                 140 aag aac cag gga atg tgc ggc tcg tgc tgg gcc ttc tcc gcc att ggc     480
Lys Asn Gln Gly Met Cys Gly Ser Cys Trp Ala Phe Ser Ala Ile Gly
145                 150                 155                 160 aac att gaa ggc cag tgg gct ttg aaa aac cac tcg ctg gtt tcg ctg     528
Asn Ile Glu Gly Gln Trp Ala Leu Lys Asn His Ser Leu Val Ser Leu
                165                 170                 175 tcg gag cag atg ctc gtg tca tgc gac gac atc gat gat ggg tgc aac     576
Ser Glu Gln Met Leu Val Ser Cys Asp Asp Ile Asp Asp Gly Cys Asn
            180                 185                 190 ggc ggg ctg atg gac cag gca atg gaa tgg atc atc cac cat cac aac     624
Gly Gly Leu Met Asp Gln Ala Met Glu Trp Ile Ile His His His Asn
        195                 200                 205 ggc act gtg ccc acg gag gaa agc tac ccc tac gcc tct gcc ggc ggc     672
Gly Thr Val Pro Thr Glu Glu Ser Tyr Pro Tyr Ala Ser Ala Gly Gly
210                 215                 220 acg agg ccg ccg tgc cat gac aaa ggc aac gtt ggc gcc aga atc ggc     720
Thr Arg Pro Pro Cys His Asp Lys Gly Asn Val Gly Ala Arg Ile Gly
225                 230                 235                 240 ggt tac atg tcc ctg ccg cat gac gag aag gag atc gcg gct tat gtg     768
Gly Tyr Met Ser Leu Pro His Asp Glu Lys Glu Ile Ala Ala Tyr Val
                245                 250                 255 gag aag aac ggc ccc gtc gcc gtc gcc gtc gac gcg aca acc tgg cag     816
Glu Lys Asn Gly Pro Val Ala Val Ala Val Asp Ala Thr Thr Trp Gln
            260                 265                 270 ctg tac ttt ggc ggt gtg gtc acc ctc tgc ttc ggg tgg tcg ctc aac     864
Leu Tyr Phe Gly Gly Val Val Thr Leu Cys Phe Gly Trp Ser Leu Asn
        275                 280                 285 cac ggt gtg ctc gtt gtc ggc ttc aac aga gac gcg aaa ccg ccg tac     912
His Gly Val Leu Val Val Gly Phe Asn Arg Asp Ala Lys Pro Pro Tyr
290                 295                 300 tgg atc gtg aag aac tcg tgg ggc acc tcg tgg ggt gag aac ggg tac     960
Trp Ile Val Lys Asn Ser Trp Gly Thr Ser Trp Gly Glu Asn Gly Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 305 |     |     |     |     | 310 |     |     |     |     | 315 |     |     | 320 |      |
| atc | cgc | ctt | gcc | atg | ggc | agc | aac | cag | tgc | ttg | ctg | aag | aat | tac | gcc | 1008 |
| Ile | Arg | Leu | Ala | Met | Gly | Ser | Asn | Gln | Cys | Leu | Leu | Lys | Asn | Tyr | Ala |      |
|     |     |     |     | 325 |     |     |     |     | 330 |     |     |     |     | 335 |     |      |
| gtg | acg | gcc | acg | ata | gac | gac | tcc | aac | acc | tcc | cac | gtg | ccg | acg | aca | 1056 |
| Val | Thr | Ala | Thr | Ile | Asp | Asp | Ser | Asn | Thr | Ser | His | Val | Pro | Thr | Thr |      |
|     |     |     | 340 |     |     |     |     | 345 |     |     |     |     | 350 |     |     |      |
| acg | gcc | tag |     |     |     |     |     |     |     |     |     |     |     |     |     | 1065 |
| Thr | Ala |     |     |     |     |     |     |     |     |     |     |     |     |     |     |      |

<210> SEQ ID NO 2
<211> LENGTH: 354
<212> TYPE: PRT
<213> ORGANISM: Leishmania infantum

<400> SEQUENCE: 2

| Met | Ala | Arg | Arg | Asn | Cys | Phe | Leu | Phe | Ala | Ile | Val | Val | Thr | Ile | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Phe | Val | Val | Cys | Tyr | Gly | Ser | Ala | Leu | Ile | Ala | Gln | Thr | Pro | Leu | Gly |
| --- | --- | --- | --- | --- | --- | --- | --- | --- | --- | --- | --- | --- | --- | --- | --- |
|     |     |     | 20  |     |     |     |     | 25  |     |     |     |     | 30  |     |     |

| Val | Asp | Asn | Phe | Ile | Ala | Ser | Ala | His | Tyr | Gly | Arg | Phe | Lys | Lys | His |
| --- | --- | --- | --- | --- | --- | --- | --- | --- | --- | --- | --- | --- | --- | --- | --- |
|     |     | 35  |     |     |     |     | 40  |     |     |     |     | 45  |     |     |     |

| His | Gly | Lys | Ala | Phe | Gly | Glu | Asp | Ala | Glu | Glu | Gly | Arg | Arg | Phe | Asn |
| --- | --- | --- | --- | --- | --- | --- | --- | --- | --- | --- | --- | --- | --- | --- | --- |
|     | 50  |     |     |     |     | 55  |     |     |     |     | 60  |     |     |     |     |

| Ala | Phe | Lys | Gln | Asn | Met | Gln | Thr | Ala | Tyr | Phe | Leu | Asn | Ala | His | Asn |
| --- | --- | --- | --- | --- | --- | --- | --- | --- | --- | --- | --- | --- | --- | --- | --- |
| 65  |     |     |     |     | 70  |     |     |     |     | 75  |     |     |     |     | 80  |

| Pro | His | Ala | His | Tyr | Asp | Val | Ser | Gly | Lys | Phe | Ala | Asp | Leu | Thr | Pro |
| --- | --- | --- | --- | --- | --- | --- | --- | --- | --- | --- | --- | --- | --- | --- | --- |
|     |     |     |     | 85  |     |     |     |     | 90  |     |     |     |     | 95  |     |

| Gln | Glu | Phe | Ala | Lys | Leu | Tyr | Leu | Asn | Pro | Asn | Tyr | Tyr | Ala | Arg | His |
| --- | --- | --- | --- | --- | --- | --- | --- | --- | --- | --- | --- | --- | --- | --- | --- |
|     |     |     | 100 |     |     |     |     | 105 |     |     |     |     | 110 |     |     |

| Gly | Lys | Asp | Tyr | Lys | Glu | His | Val | His | Val | Asp | Asp | Ser | Val | Arg | Ser |
| --- | --- | --- | --- | --- | --- | --- | --- | --- | --- | --- | --- | --- | --- | --- | --- |
|     |     | 115 |     |     |     |     | 120 |     |     |     |     | 125 |     |     |     |

| Gly | Val | Met | Ser | Leu | Asp | Trp | Arg | Glu | Lys | Gly | Ala | Val | Thr | Pro | Val |
| --- | --- | --- | --- | --- | --- | --- | --- | --- | --- | --- | --- | --- | --- | --- | --- |
|     | 130 |     |     |     |     | 135 |     |     |     |     | 140 |     |     |     |     |

| Lys | Asn | Gln | Gly | Met | Cys | Gly | Ser | Cys | Trp | Ala | Phe | Ser | Ala | Ile | Gly |
| --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |

| Asn | Ile | Glu | Gly | Gln | Trp | Ala | Leu | Lys | Asn | His | Ser | Leu | Val | Ser | Leu |
| --- | --- | --- | --- | --- | --- | --- | --- | --- | --- | --- | --- | --- | --- | --- | --- |
|     |     |     |     | 165 |     |     |     |     | 170 |     |     |     |     | 175 |     |

| Ser | Glu | Gln | Met | Leu | Val | Ser | Cys | Asp | Asp | Ile | Asp | Asp | Gly | Cys | Asn |
| --- | --- | --- | --- | --- | --- | --- | --- | --- | --- | --- | --- | --- | --- | --- | --- |
|     |     |     | 180 |     |     |     |     | 185 |     |     |     |     | 190 |     |     |

| Gly | Gly | Leu | Met | Asp | Gln | Ala | Met | Glu | Trp | Ile | Ile | His | His | His | Asn |
| --- | --- | --- | --- | --- | --- | --- | --- | --- | --- | --- | --- | --- | --- | --- | --- |
|     |     | 195 |     |     |     |     | 200 |     |     |     |     | 205 |     |     |     |

| Gly | Thr | Val | Pro | Thr | Glu | Glu | Ser | Tyr | Pro | Tyr | Ala | Ser | Ala | Gly | Gly |
| --- | --- | --- | --- | --- | --- | --- | --- | --- | --- | --- | --- | --- | --- | --- | --- |
|     | 210 |     |     |     |     | 215 |     |     |     |     | 220 |     |     |     |     |

| Thr | Arg | Pro | Pro | Cys | His | Asp | Lys | Gly | Asn | Val | Gly | Ala | Arg | Ile | Gly |
| --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |

| Gly | Tyr | Met | Ser | Leu | Pro | His | Asp | Glu | Lys | Glu | Ile | Ala | Ala | Tyr | Val |
| --- | --- | --- | --- | --- | --- | --- | --- | --- | --- | --- | --- | --- | --- | --- | --- |
|     |     |     |     | 245 |     |     |     |     | 250 |     |     |     |     | 255 |     |

| Glu | Lys | Asn | Gly | Pro | Val | Ala | Val | Ala | Val | Asp | Ala | Thr | Thr | Trp | Gln |
| --- | --- | --- | --- | --- | --- | --- | --- | --- | --- | --- | --- | --- | --- | --- | --- |
|     |     |     | 260 |     |     |     |     | 265 |     |     |     |     | 270 |     |     |

| Leu | Tyr | Phe | Gly | Val | Val | Thr | Leu | Cys | Phe | Gly | Trp | Ser | Leu | Asn |
| --- | --- | --- | --- | --- | --- | --- | --- | --- | --- | --- | --- | --- | --- | --- |
|     |     | 275 |     |     |     |     | 280 |     |     |     |     | 285 |     |     |

| His | Gly | Val | Leu | Val | Val | Gly | Phe | Asn | Arg | Asp | Ala | Lys | Pro | Pro | Tyr |
| --- | --- | --- | --- | --- | --- | --- | --- | --- | --- | --- | --- | --- | --- | --- | --- |
|     | 290 |     |     |     |     | 295 |     |     |     |     | 300 |     |     |     |     |

| Trp | Ile | Val | Lys | Asn | Ser | Trp | Gly | Thr | Ser | Trp | Gly | Glu | Asn | Gly | Tyr |
| --- | --- | --- | --- | --- | --- | --- | --- | --- | --- | --- | --- | --- | --- | --- | --- |

305            310             315              320
Ile Arg Leu Ala Met Gly Ser Asn Gln Cys Leu Leu Lys Asn Tyr Ala
            325             330              335

Val Thr Ala Thr Ile Asp Asp Ser Asn Thr Ser His Val Pro Thr Thr
            340             345              350

Thr Ala

<210> SEQ ID NO 3
<211> LENGTH: 1329
<212> TYPE: DNA
<213> ORGANISM: Leishmania infantum
<220> FEATURE:
<221> NAME/KEY: Unsure
<222> LOCATION: (433)..(796)
<223> OTHER INFORMATION: "n" represents unknown sequence.

<400> SEQUENCE: 3

```
atggcgacgt cgagggccgc tctttgcgct gttgcggttg tgtgcgtggt gcttgcggct      60
gcctgcgcgc ccgcgcgcgc gatatacgtg gggacgccgg ctgctgcgct gttcgaggag     120
ttcaagcgga cgtaccggcg cgcgtacggg acggtggccg aggagcagca gcggctggcg     180
aacttcgagc gcaacctgga gctgatgcgc gagcatcagg cgaggaaccc acacgcgagg     240
ttcgggatca cgaagttctt cgacctgtcg gaggcggagt cgccgcgcg ctacctgaac      300
ggcgccgcgt acttcgcagc ggcgaagcag cacgccggcc agcactaccg caaggcgcgc    360
gcggacctgt cggcggtgcc tgatgcggtg gactggcgca agaagggcgc cgtgacgccg    420
gtgaaggatc cgnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnccag ctccttcatg tcctaccaga gcggcgtgct gaccagctgc    840
gctgggatg ctctgaacca cggcgtgctg ctcgttgggt acaacaggac tggtgaggtt     900
ccgtactggg tgatcaagaa ctcgtggggt gaggactggg gcgagaacgg ctacgtgcgc    960
gtgaccatgg gggtgaacgc gtgcctgctc actgaatacc ccgtgtccgc gcatgtgccg   1020
cagagtccca cccctggccc gagcacggag agcgaggagc gcgctccaaa acgggtgatg   1080
gtggagcaga taatctgcac ggatatgtac tgcaggagg ggtgcaggaa gactcttctc   1140
accgcgaacg tgtgccagct gaacggggga ggcggctcct ctatgaccaa gtgcagtccg   1200
cacaaggtgc tgatgtgcac gtactcgaac cctcgttgct ttggtccggg gctttgcctc   1260
gagactcctg atggtaagtg tgcgccgtac ttcttgggct cggtcactaa cacctgccag   1320
tacacgtag                                                           1329
```

<210> SEQ ID NO 4
<211> LENGTH: 442
<212> TYPE: PRT
<213> ORGANISM: Leishmania infantum
<220> FEATURE:
<221> NAME/KEY: UNSURE
<222> LOCATION: (145)..(266)
<223> OTHER INFORMATION: "Xaa" represents unknown sequence

<400> SEQUENCE: 4

```
Met Ala Thr Ser Arg Ala Ala Leu Cys Ala Val Ala Val Cys Val
1               5                   10                  15

Val Leu Ala Ala Ala Cys Ala Pro Ala Arg Ala Ile Tyr Val Gly Thr
            20                  25                  30

Pro Ala Ala Leu Phe Glu Glu Phe Lys Arg Thr Tyr Arg Arg Ala
        35                  40                  45

Tyr Gly Thr Val Ala Glu Glu Gln Gln Arg Leu Ala Asn Phe Glu Arg
    50                  55                      60

Asn Leu Glu Leu Met Arg Glu His Gln Ala Arg Asn Pro His Ala Arg
65                  70                  75                  80

Phe Gly Ile Thr Lys Phe Phe Asp Leu Ser Glu Ala Glu Phe Ala Ala
                85                  90                  95

Arg Tyr Leu Asn Gly Ala Ala Tyr Phe Ala Ala Lys Gln His Ala
                100                 105                 110

Gly Gln His Tyr Arg Lys Ala Arg Ala Asp Leu Ser Ala Val Pro Asp
        115                 120                 125

Ala Val Asp Trp Arg Lys Lys Gly Ala Val Thr Pro Val Lys Asp Pro
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Ser Ser Phe Met Ser Tyr
                260                 265                 270

Gln Ser Gly Val Leu Thr Ser Cys Ala Gly Asp Ala Leu Asn His Gly
        275                 280                 285

Val Leu Leu Val Gly Tyr Asn Arg Thr Gly Glu Val Pro Tyr Trp Val
        290                 295                 300

Ile Lys Asn Ser Trp Gly Glu Asp Trp Gly Glu Asn Gly Tyr Val Arg
305                 310                 315                 320

Val Thr Met Gly Val Asn Ala Cys Leu Leu Thr Glu Tyr Pro Val Ser
                325                 330                 335

Ala His Val Pro Gln Ser Pro Thr Pro Gly Pro Ser Thr Glu Ser Glu
            340                 345                 350

Glu Arg Ala Pro Lys Arg Val Met Val Glu Gln Ile Ile Cys Thr Asp
        355                 360                 365

Met Tyr Cys Arg Glu Gly Cys Met Lys Thr Leu Leu Thr Ala Asn Val
    370                 375                 380

Cys Gln Leu Asn Gly Gly Gly Ser Ser Met Thr Lys Cys Gly Pro
385                 390                 395                 400

His Lys Val Leu Met Cys Thr Tyr Ser Asn Pro Arg Cys Phe Gly Pro
                405                 410                 415
```

```
Gly Leu Cys Leu Glu Thr Pro Asp Gly Lys Cys Ala Pro Tyr Phe Leu
            420                 425                 430

Gly Ser Val Thr Asn Thr Cys Gln Tyr Thr
            435                 440
```

<210> SEQ ID NO 5
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: oligonucleotide primer

<400> SEQUENCE: 5
ggatccgcct gcgcacctgc gcgcgcga                28

<210> SEQ ID NO 6
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: oligonucleotide primer

<400> SEQUENCE: 6
aagcttctac cgcacatgcg cggacacgg                29

<210> SEQ ID NO 7
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: oligonucleotide primer

<400> SEQUENCE: 7
ggtgcgtgcg ggtcggctgg gcgttctcgg                30

<210> SEQ ID NO 8
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: oligonucleotide primer

<400> SEQUENCE: 8
gcccgagtgc tcgagcagca gtgagctcg                29

<210> SEQ ID NO 9
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: oligonucleotide primer

<400> SEQUENCE: 9
gacgccggtg aagaatcagg gtgcgtg                27

<210> SEQ ID NO 10
<211> LENGTH: 29

```
-continued

<212> TYPE: DNA
<213> ORGANISM: Artificial Sequence
<220> FEATURE:
<221> NAME/KEY: misc_feature
<222> LOCATION: (1)..(29)
<223> OTHER INFORMATION: oligonucleotide primer

<400> SEQUENCE: 10
cgaacgggca cctgtacacg gaggacagc                                       29

<210> SEQ ID NO 11
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: oligonucleotide primer

<400> SEQUENCE: 11
gctgcgatga catgaacgat ggttgcgacg gcgggctgat gc                        42

<210> SEQ ID NO 12
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: oligonucleotide primer

<400> SEQUENCE: 12
gtgcgagctg tggcctctgc gt                                              22

<210> SEQ ID NO 13
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: oligonucleotide primer

<400> SEQUENCE: 13
ggcgcgcgcg cacccaagg                                                  19
```